United States Patent
Sonnenschein

(10) Patent No.: US 6,238,706 B1
(45) Date of Patent: May 29, 2001

(54) METHOD OF STIMULATING GROWTH IN AQUATIC ANIMALS USING GROWTH HORMONES

(75) Inventor: Leonard Sonnenschein, Ballwin, MO (US)

(73) Assignee: GroFish L.L.C., Brentwood, MO (US)

(*) Notice: Subject to any disclaimer, the term of this patent is extended or adjusted under 35 U.S.C. 154(b) by 0 days.

(21) Appl. No.: 09/427,532

(22) Filed: Oct. 26, 1999

Related U.S. Application Data
(60) Provisional application No. 60/132,933, filed on May 6, 1999.

(51) Int. Cl.[7] .......................... A61K 35/55; A61K 35/12; A61K 38/00
(52) U.S. Cl. .......................... 424/562; 424/520; 424/565; 514/2; 514/21
(58) Field of Search ..................................... 424/520, 562, 424/565; 514/2, 21

(56) References Cited

U.S. PATENT DOCUMENTS

| | | |
|---|---|---|
| 4,041,180 | 8/1977 | Wilson . |
| 4,848,275 | 7/1989 | Swanson . |
| 4,863,736 | 9/1989 | Azain et al. . |
| 5,089,473 | 2/1992 | Krivi et al. . |
| 5,350,543 | 9/1994 | Spradley . |
| 5,474,980 | 12/1995 | Mitchell . |
| 5,691,277 | 11/1997 | Estienne et al. . |
| 5,735,934 | 4/1998 | Spears . |
| 5,893,838 | 4/1999 | Daoud et al. . |
| 6,017,447 | 1/2000 | Wright et al. . |

OTHER PUBLICATIONS

Caldwell et al. Journal of Aquatic Animal Health, vol. 7, No. 2, pp. 168–171, 1995.*

Edsall et al. The Progressive Fish–Culturist, vol. 53, pp. 95–97, 1991.*

Seafood International, vol. 6, No. 12, p. 48, 1991.*

Schulte, Down, Donaldson and Souza/Experimental Administration of Recombinant Bovine Growth Hormone to Juvenile Rainbow Trout (*Salmo gairdneri*) by Injection or by Immersion/Aquaculture, 76 (1989) pp. 145–156/Elsevier Science Publishers, b.V., Amsterdam–Netherlands.

S. Moriyama and H. Kawauchi/"Growth Stimulation of Juvenile Salmonids by Immersion in Recombinant Salmon Growth Hormone"/Nippon Suisan Gakkaishi 56(1), pp. 31–34 (1990).

Agellon et al., "Promotion Of Rapid Growth Of Rainbow Trout (*Salmo gairdneri* by a Recombinant Fish Growth Hormone" Can. J. Fish. Aqua. Sci., vol. 45 (1988) pp. 146–151.

\* cited by examiner

*Primary Examiner*—Francisco Prats
*Assistant Examiner*—Susan D. Coe
(74) *Attorney, Agent, or Firm*—Polster, Lieder, Woodruff & Lucchesi

(57) ABSTRACT

A method of administering growth hormone includes (a) osmotically shocking aquatic animals for about 60 seconds with a hyperosmotic salt solution; and (b) placing the shocked aquatic animals in a tank containing a solution of about 300 mg/l of growth hormone (preferably bST). The treatment solution is preferably at least slightly saline. The aquatic animals are immersed in the treatment solution for between about 30 minutes and about two hours. The growth hormone solution is supersaturated with oxygen to place the aquatic animals in a state of suspended animation. Depending on the aquatic species treated, the osmotic salt solution and the treatment solution may be refrigerated. The aquatic animals are preferably treated when less than 24 hours old.

23 Claims, 19 Drawing Sheets

METHOD OF STIMULATING GROWTH IN AQUATIC ANIMALS USING GROWTH HORMONES

CROSS-REFERENCE TO RELATED APPLICATIONS

This application is related to provisional application Serial No. 60/132,933 filed May 6, 1999 entitled Use Of Bovine Somatotropin To Enhance Fish Growth.

STATEMENT REGARDING FEDERALLY SPONSORED RESEARCH OR DEVELOPMENT

Not Applicable.

BACKGROUND OF THE INVENTION

This invention relates to aquaculture, and, in particular, to the use of growth hormones, especially bovine somatotropin (bST), to enhance the rate at which aquatic animals grow.

Fish is a recognized source of food. World-wide demand for wild-caught fish has lead to a phenomenal growth in the aquaculture industry. World-wide demand for fish continues to grow. Fish are found world wide, and can be fairly inexpensive where fish are plentiful. If fish could be grown more quickly, farm grown fish could be harvested more quickly than presently possible. This could increase the supply of fish and concomitantly reduce the cost of fish to consumers and reduce the threat of over fishing of wild populations of fish and the effects on the environment of such over fishing. A considerable amount of research has been conducted with aquatic animals, and in particular, with methods or treatments to increase the rate of growth of aquatic animals. Some of this research has focused on the use of growth hormones (including bST) and methods of administering growth hormones to fish. Fish have been injected with growth hormones and immersed in growth hormone solutions. Because of the configuration of fish muscles and skin, the skin does not readily close up at the injection site, and hormones injected subdermally or intramuscularly can simply be washed out of the fish. The injection of bST into fish thus has not been a successful method of administering growth hormones.

I know of two studies in which fish were treated with growth hormones: (1) Growth Stimulation of Juvenile Salmonids by Immersion in Recombinant Salmon Growth Hormone, Moriyama et al., *Nippon Suisan Gakaishi*, 56(1):31–34 (1990); and (2) Experimental Administration of Recombinant Bovine Growth Hormone To Juvenile Rainbow Trout (Salmo Gairdineri) By Injection Or By Immersion, Schulte, et. al., *Aquaculture*, 76:145–156 (1989). Both studies used low levels of growth hormone. In the former study fish were immersed in a solution containing 30 mg/l of BSA; in the latter study, fish were injected with 10 μg growth hormone/g body weight. The method disclosed in the latter study (Schulte, et. al.) did not show a marked difference between the treated and control groups. In the former study, the authors concluded that immersion in rsGH may be useful as a method of GH (growth hormone) administration to accelerate the growth of fish in aquaculture. However, there are advances that can still be made in the administration of growth hormones to fish, particularly in the manner of administration of the growth hormone to enhance or accelerate the growth of fish.

BRIEF SUMMARY OF THE INVENTION

A method of increasing the rate of growth of aquatic animals comprises immersing the aquatic animal in a solution of growth hormone. When immersed in the growth hormone solution, the aquatic animal swallows the solution, and the growth hormone is absorbed through the aquatic animal's gut, rather than through its skin, muscle, or gills. The administration of growth hormones to the aquatic animals is believed to increase the animals' metabolism and thus stimulate growth. The increased rate of growth is accomplished using natural products (or synthesized copies of the natural products). The genetic phenotype or the cellular consistency of the aquatic animal is not altered.

The growth hormone solution (or treatment solution) contains 3–3000 mg growth hormone per liter. Preferably, the solution contains 150–450 mg, and most preferably 300 mg growth hormone solution per liter. The growth hormone is bST, although other related growth hormones should work equally as well. Additionally, the treatment solution includes at least some salt to make the solution at least slightly saline. The growth hormone solution is supersaturated with oxygen to enable the aquatic animals to be treated for longer periods of time. This places the aquatic animal in a state of suspended animation. Prior to immersing the aquatic animal in the growth hormone solution, the aquatic animals are osmotically shocked in a higher concentration, hyperosmotic, saline solution. The salinity of the shocking solution depends on the aquatic animal being shocked. The salinity of the treatment solution is preferably about one-half that of the shocking solution. The growth hormone solution, depending on the aquatic animal being treated, can be refrigerated. The aquatic animals are immersed in the treatment solution for between two minutes and six hours. Preferably, the immersion time is 30 minutes to 2 hours, and most preferably about one to one-and-one half hours. After the treatment period has elapsed, the temperature of the aquatic animal is slowly raised to an ambient temperature, for example, by titrating the growth hormone solution with warmer water.

The aquatic animals are preferably treated at any time up to about six-months of age. Preferably, however, the aquatic animals are treated when young, i.e., less than nine days old, and more preferably, when less than twenty-four hours old.

DETAILED DESCRIPTION OF THE INVENTION

Figure 1:
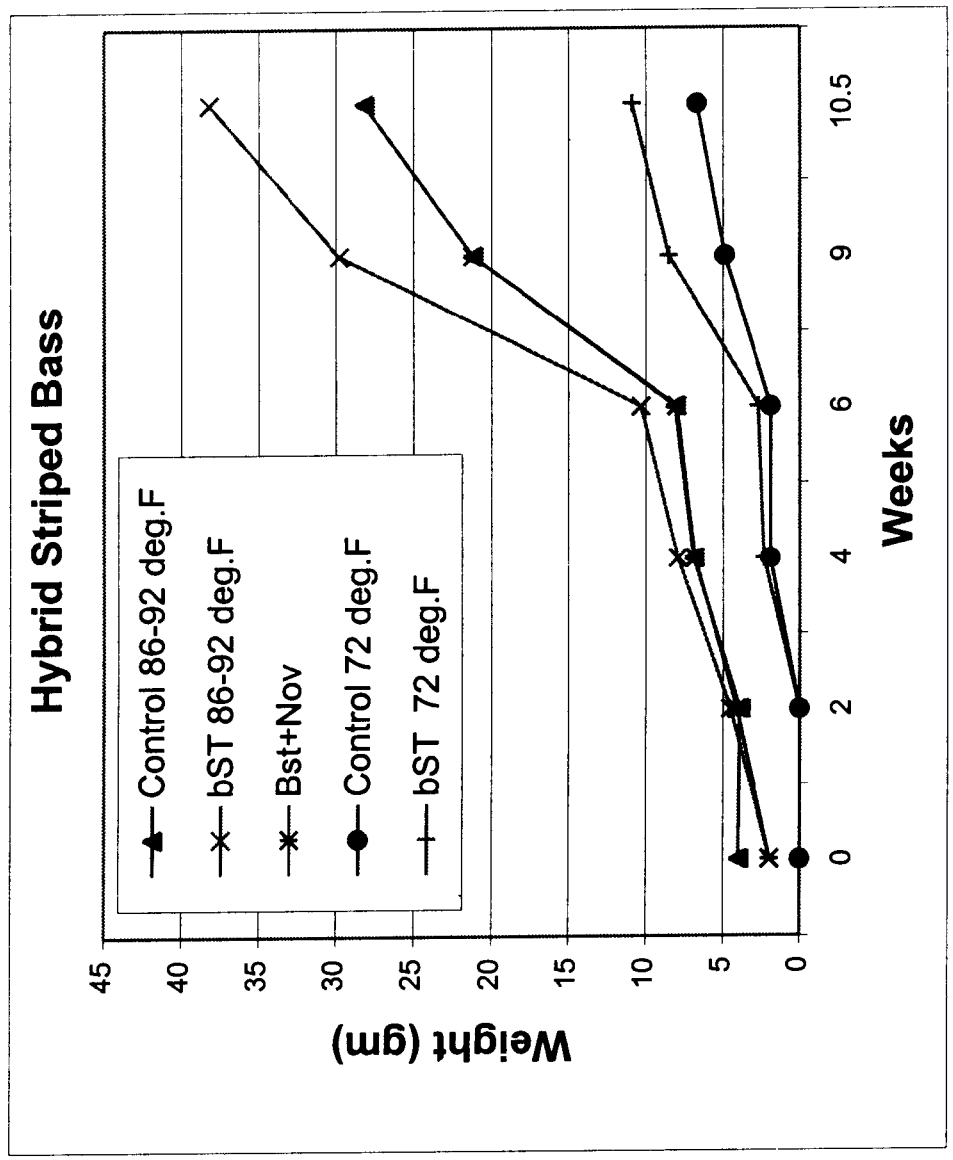
FIG. 1 is a chart showing the results of treating hybrid striped bass in accordance with the invention.

The following detailed description illustrates the invention by way of example and not by way of limitation. This description will clearly enable one skilled in the art to use the invention, and describes what I presently believe is the best mode of carrying out the invention.

The method of treating aquatic animals with growth hormones, namely, bST, was studied in association with hybrid striped bass, channel catfish, fresh water prawns, shrimp, carp, and salmon, as discussed below. I believe that the treatment will work on other aquatic animals equally as well. For example, the treatment should work with Talapia and other bass species, other carp species, other invertebrates, such as lobsters, crabs, abalone, etc., and other aquatic vertebrates, such as amphibians. The treatment involved immersing the aquatic animal in a bST solution for a period of time. The concentration of bST in the solution varied from 3 mg/l to 3000 mg/l, preferably about 150 mg/l to about 450 mg/l, and most preferably about 300 mg/l. The immersion time of the aquatic animal in the solution varied from approximately 2 minutes to about 6 hours; preferably from about 30 minutes to about 180 minutes; and most preferably, from about 60 minutes to 120 minutes. The bST solution was supersaturated with oxygen to place the aquatic animal in suspended animation while they were immersed in the bST solution. The treatment solution included some NaCl, so that the bST solution was at least somewhat saline. Different aquatic animals respond differently to water temperature and water salinity. Thus the protocols for the different aquatic animals had to be varied to account for this. Statistical studies done for the data sets where change was evident using a T-test evaluation consistently indicated that the data was statistically significant for change due to the treatment, with a $p<0.05$.

Additionally, prior to placing the aquatic animals (except for shrimp and prawns) in the treatment solution, the aquatic animals were osmotically shocked by placing them in a hyperosmotic saline solution. The saline solution used to osmotically shock the aquatic animal typically had a salinity of about twice the salinity of the treatment solution. As discussed below, the shrimp and prawns were received in saline solutions, and thus were already osmotically shocked.

The Basic Treatment Procedure for Bass, Carp, and Prawns

The treatment for the hybrid striped bass involved osmotically shocking the fish by immersing them in a cold (approximately 45° F.) hyperosmotic saline solution for about 120 seconds. The saline solution was about 0.375–1.5M NaCl, and preferably about 1.5M NaCl. They were then immersed in the bST solution (about 300 mg bST/l) for about one hour. The bST solution was cold (approximately 45° F.). It was also slightly saline, the solution being about 0.1 5–0.75M NaCl (and preferably about 0.75M NaCl). For the hybrid striped bass, the salinity of the bST solution was less than the salinity of the shock solution. The treatment tank was closed, and while the fish were in the treatment tank, oxygen was bubbled into the tank, so that the water was supersaturated with oxygen. Some fish were treated only once, others were treated twice. While other fish were treated every two weeks. After each treatment session, the fish were placed in holding tanks, the temperatures of which were approximately equal to the ambient temperature of the tank's surroundings.

The catfish were highly susceptible to temperature and salinity of the solution in which they were kept. If the solution was too cold and/or too salty, they would die. Thus, the protocol for the catfish had to be altered from the striped bass protocol to account for the catfish's susceptibility to salinity and temperature. The treatment of the catfish involved osmotically shocking the catfish by immersing them in a saline solution at room temperature for about 2 minutes. The shocking solution was about 0.75M NaCl. The fish were then moved to treatment tanks, where the fish were immersed in the bST solution at room temperature for about one hour. The bST solution contained about 300 mg bST/l, was about 0.375M NaCl, and was supersaturated with oxygen.

The prawns were received in a cold saline solution which had a specific gravity of 1.002 and a temperature of 45° F.–55° F. Thus, upon receipt of the prawns, they were placed directly in the bST solution for a single treatment for a period of one hour. The bST solution was saltier than the solution in which the prawns were received. In this case, the treatment solution contained about 300 mg/l bST, had a specific gravity of 1.010, a temperature of about 45° F., and was supersaturated with oxygen.

EXAMPLE 1

Treatment of Hybrid Striped Bass

The protocol for treating hybrid striped bass involved osmotically shocking the fish with a refrigerated osmotic salt solution for about 120 seconds. The salt solution was about 1.5M NaCl. The temperature of the salt solution was about 45° F. The shocked fish were then transferred to a tank containing a refrigerated solution of growth hormone. Preferably, bovine somatotropin (bST) is used and is at a normal saline content (about 0.75M NaCl). The solution contained about 300 mg bST/l. The bST tank was closed, and the bST solution in the tank, with the fish therein, was supersaturated with oxygen by bubbling oxygen into the solution. Supersaturating the water with oxygen is believed to place the fish in a state of suspended animation, and allows the fish to be treated for longer periods of time. The fish remain in the refrigerated, oxygenated bST solution for about one hour. After the treatment period is over (i.e., after about one hour), the temperature of the bST solution was slowly increased to room temperature. Preferably, this is done over a fifteen minute period by titrating the bST solution with warmer (room temperature) water. The water cannot be increased in temperature too quickly, and the water was raised to normal room temperature (68° F.) at a rate of about 1.5° F./minute. This treatment procedure was carried out approximately every two weeks for 10½ weeks. As seen in FIG. 1 and Table I below, the treatment resulted in significant increases in the growth rate of the fish, as compared to a control group of the fish.

The hybrid striped bass were divided into 5 categories: (1) a control group wherein the water was warm (86–92° F.); (2) a group treated with bST as noted above wherein the water was warm (86–92° F.); (3) a group treated with bST and NovAqua® and wherein the water was warm; (4) a control group wherein the water was maintained at room temperature (i.e., about 72° F.); and (5) a group treated with bST wherein the water was maintained at room temperature (i.e., about 72° F.). NovAqua® is a water conditioner available from the Kordon division of Novalek of Hayward, Calif., which contains a buffering system, synthetic polymers, reducing agents (dechlorinators), electrolytes, and stabilizers. It provides a colloid coating on the fish's body. It is known that NovAqua® will compete with, and interfere with, the binding of bST to the fish. Thus, the NovAqua® should prevent the bST from affecting the growth of the fish. The third group thus measured the effect of the osmotic shock and immersion in water supersaturated with oxygen on the growth of the fish. As seen in Table I below, the fish treated with both bST and NovAqua grew at substantially the same rate as the control fish. This shows that the growth of the bST treated fish was due to the bST, and that the osmotic shock and the oxygen supersaturated water did not, by themselves, attribute to the enhanced growth rate of the fish. Additionally, it can be seen from the data and the chart of FIG. 1 that the fish kept in the warmer bath water grew at a faster rate than the fish in the colder water. The control group had 40 fish and the bST and bST+NovAqua groups each had 50 fish. The weight of the fish were monitored for 10½ weeks. The fish were treated every two weeks, and in between treatments, the fish were held in holding tanks.

TABLE I

Average Weight of Hybrid Striped Bass in Grams

| | Warm Water Bath (86–92° F.) | | | Room Temp. Water (~72° F.) | |
|---|---|---|---|---|---|
| Week | Control | bST | bST + NovAqua | Control | bST treated |
| 0 | 1.96 | 1.96 | 1.96 | 0 | 0 |
| 2 | 3.9 | 4.5 | 4.1 | 0 | 0 |
| 4 | 6.9 | 7.9 | 6.8 | 1.9 | 2.3 |
| 6 | 8.1 | 10.3 | 8 | 1.9 | 2.7 |
| 9 | 21.2 | 29.8 | 21.2 | 4.9 | 8.5 |
| 10½ | 28.2 | 38.2 | | 6.7 | 10.9 |

The fish in the control group grew by about 1339%, whereas the bST treated fish grew by about 1849%. At the end of the 10½ weeks, the bST treated fish were 35.5% heavier than the fish in the control group. Analysis of the results using a T-test showed that the data had a p<0.05 statistical significance.

For the first 6 weeks of the experiment, the fish were housed in indoor holding tanks. At week 6, (which was in early August in St. Louis, Mo., USA), the fish were moved to outdoor holding tanks. As can be seen from FIG. 1 (which charts the data of Table I), at week 6, the fish began to grow at a much faster rate than in the prior weeks. This is believed to be due to the fact that the water in the outdoor holding tanks was warmer than the water in the indoor holding tanks. The ambient outdoor summer temperature (80–84° F.) is believed to have been an ideal temperature for the growth of the fish, and, as can be seen, the rate of growth of both the control fish and the bST treated fish was much faster than in the first six weeks, when the fish were in indoor holding tanks.

EXAMPLE II

Treatment of Channel Catfish

The channel catfish were treated somewhat similarly to the hybrid striped bass. The fish were removed from their holding tanks and osmotically shocked with a 0.75M NaCl solution for about two minutes. The shocking solution was at ambient temperature, typically about 70° F.–80° F. The catfish were then moved to the bST treatment solution. The solution had 300 mg bST/l and was 0.375M NaCl. The bST solution was also at ambient room temperature. The catfish were immersed in the bST solution for about one hour. As with the striped bass, the bST tank was closed, and the bST solution in the tank, with the fish therein, is supersaturated with oxygen to place the fish in a state of suspended animation.

Figure 2:
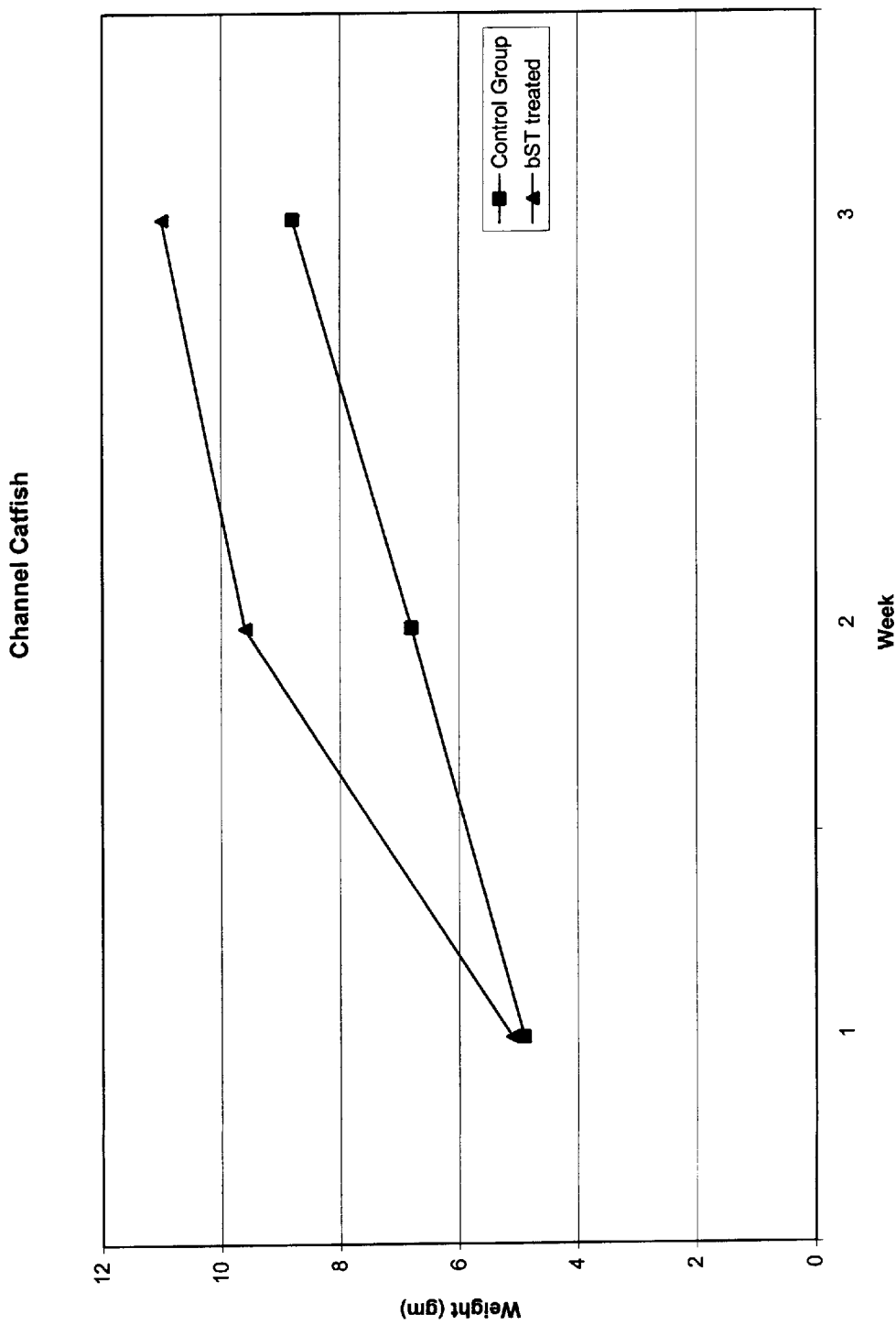
FIG. 2 is a chart showing the results of treating channel catfish in accordance with the invention.

The fish were weighed and treated at 0 weeks. The fish were kept in outdoor holding tanks in water that was about 80–84° F. The fish were weighed at two and three weeks, however, they were not treated again. As seen in FIG. 2, and in Table II below, the bST treated group grew at a rate significantly faster than the control group.

TABLE II

Average Weight of Channel Catfish in grams

| Week | Control Group | bST treated |
|---|---|---|
| 0 | 4.9 | 5.1 |
| 2 | 6.8 | 9.6 |
| 3 | 8.8 | 11.0 |

Over the three week period, the control group grew on average by about 80%, whereas, over the same period, the bST treated group grew on average by about 116%. After tlu-ee weeks, the fish in the bST treated group was, on average, about 45% heavier than the fish in the control group. Analysis of the results using a T-test showed that the data had a p<0.05, statistical significance.

EXAMPLE III

Treatment of Fresh Water Prawns

The prawns were received in a cold saline solution which had a specific gravity of about 1.002 and a temperature of about 45° F.–55° F. The prawns were already osmotically shocked. They were taken from their cold saline solution and placed directly in a refrigerated (about 45° F.–55° F.) treatment solution of 300 mg bST/l. The treatment solution had a specific gravity of 1.010 at about 45° F., and was thus approximately five times saltier than the shipping solution. The prawns were left in the treatment solution for about one hour. As with the striped bass, the bST tank was closed, and the bST solution was supersaturated with oxygen to place the prawns in a state of suspended animation. After the treatment period ended, the treatment solution was allowed to slowly warm up to room temperature, and the prawns were then placed in a fresh water outdoor holding tank (about 80–84° F.). The growth of the prawns was observed for five weeks. The prawns were treated only the one time.

Figure 3:
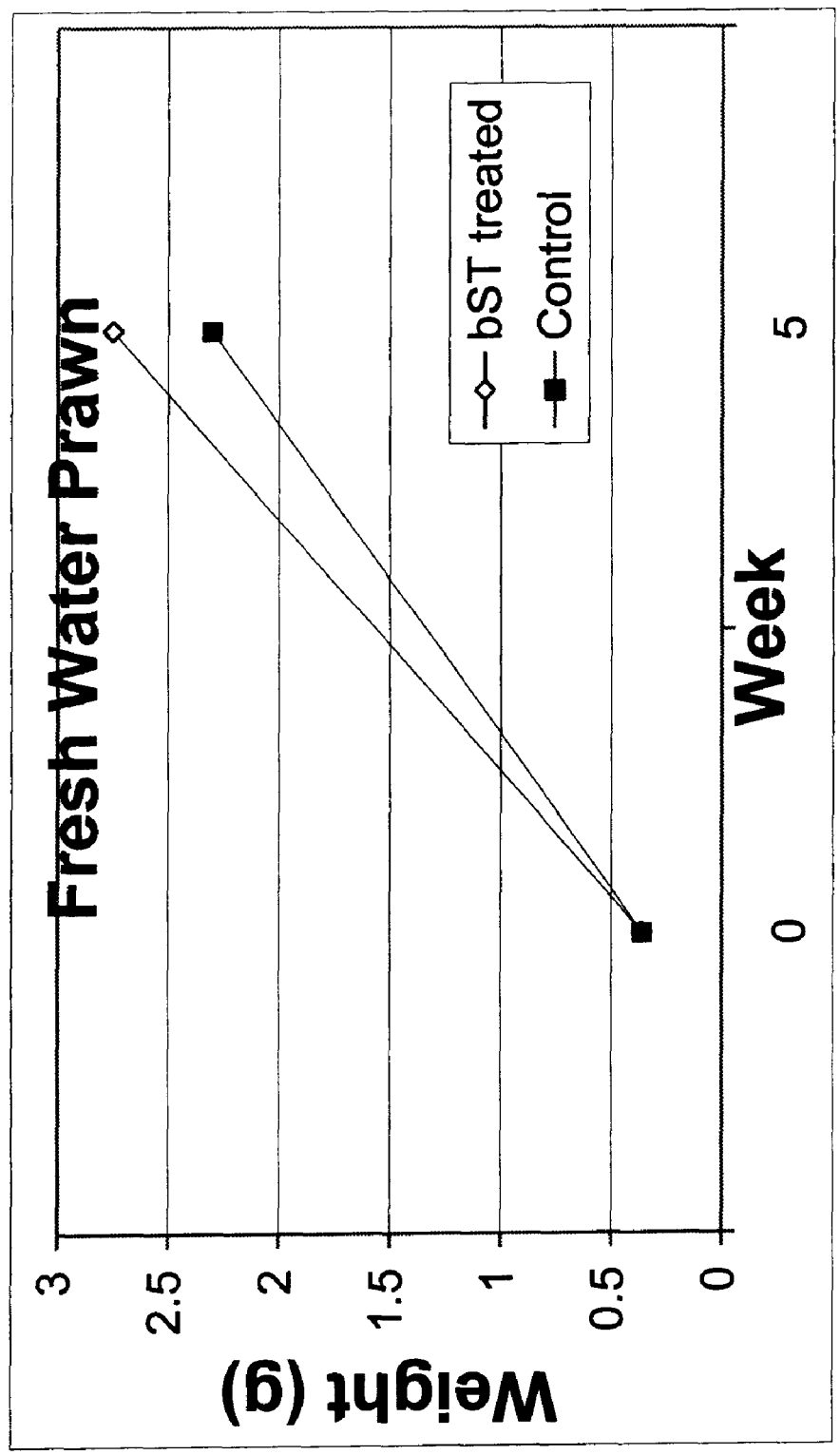
FIG. 3 is a chart showing the results of treating prawns in accordance with the invention.

As seen in FIG. 3 and Table III below, the treated prawns grew at a faster rate than the untreated control prawns. In the five week period, the control prawns grew by about 539%, whereas the bST treated prawns grew by about 664%. After five weeks, the bST treated prawns had an average weight which was about 20% greater than the prawns in the control group. Analysis of the results using a T-test showed that the data had a $p<0.01$, statistical significance.

TABLE III

Average Weight of Prawns in grams

| Week | Control | bST treated |
|---|---|---|
| 0 | 0.36 | 0.36 |
| 5 | 2.30 | 2.75 |

EXAMPLE IV

Effect Of Sonicating Fish During Treatment

Figure 4:
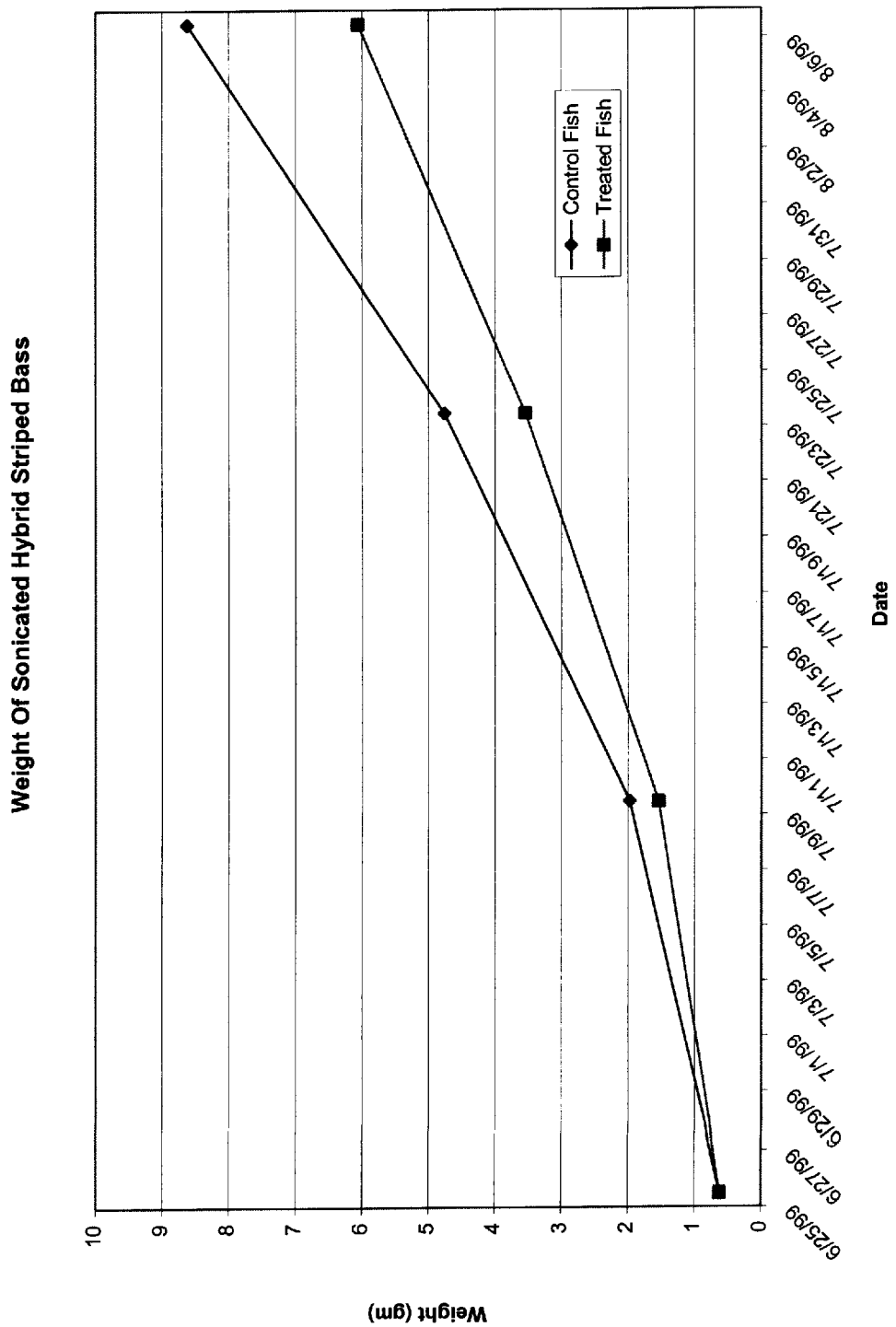
FIG. 4 is a chart showing the results of treatment of bass, when the bass were sonicated during immersion in the growth hormone solution.

In this example, bass were treated with a 300 mg/l bST solution, substantially the same as set forth in Example I. However, while immersed in the bST solution, the fish were sonicated. The fish were immersed and sonicated for about two minutes. Thus, instead of a one-hour immersion, the fish were only immersed in the bST solution for two minutes. It was found that sonication of the fish for much longer than two minutes was detrimental to the health of the fish. The sonication of the fish was intended to shock the bST into the dermal cells and gills of the fish to facilitate absorption of the bST at the skin and gill level. The results are tabulated below in Table IV, and shown in FIG. 4.

TABLE IV

Weight of Sonicated Fish v. Control Fish

| Date | Weight of Control Fish (gms) | Weight of Treated Fish (gms) |
|---|---|---|
| 6/25/99 | 0.62 | 0.62 |
| 7/9/99 | 1.97 | 1.54 |
| 7/23/99 | 4.76 | 3.54 |
| 8/6/99 | 8.62 | 6.06 |

As can be seen from the results, the control fish (which were not treated with bST) grew faster than the treated fish. These results are believed to show that the bST is not absorbed at the cutaneous (skin) or gill level. Thus, it is believed that the fish are swallowing the bST solution while immersed in the treatment solution, and that the bST itself is absorbed in the fish's (or aquatic animal's) gut.

EXAMPLE V

Treatment of Grass Carp

Figure 5A:
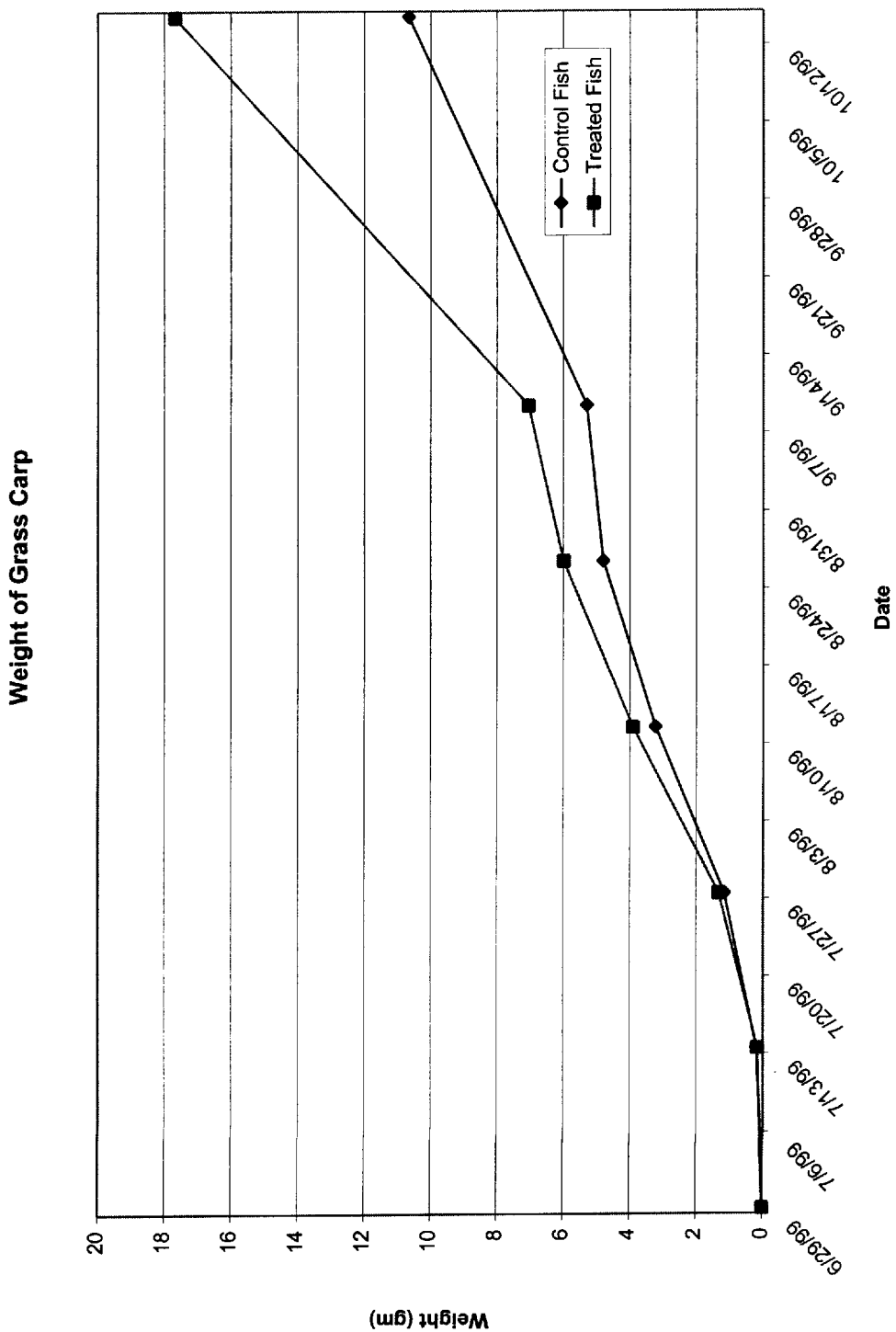
FIGS. 5A and 5B are charts showing the weight and length of grass carp treated with a growth honnone solution of 300 mg growth hormone/liter.
Figure 5B:
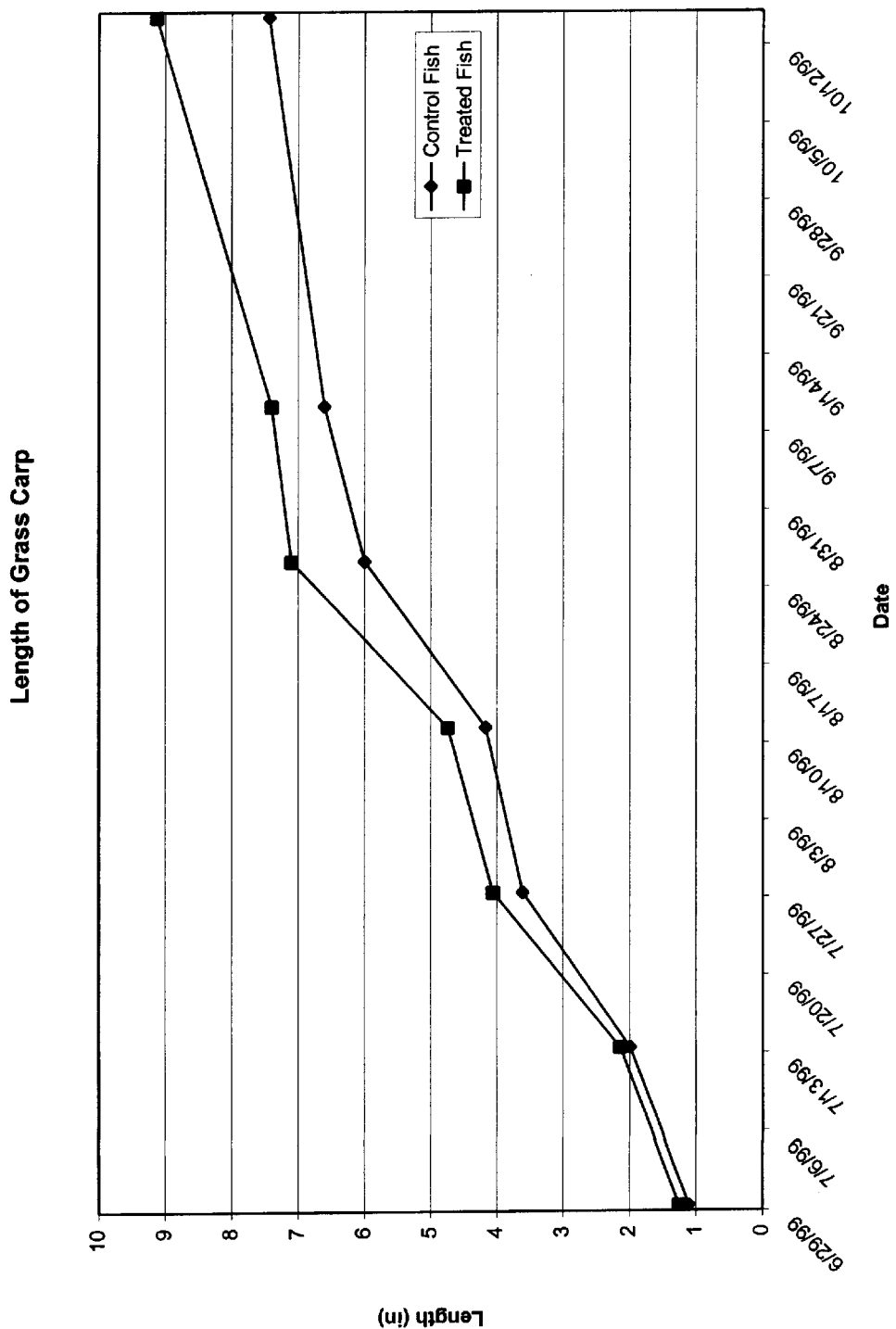

Grass carp were treated substantially in accordance with Example I, except as indicated below. The carp were initially osmotically shocked in a 0.375 molar saline solution. The shocked fish were then immersed in a 0.154 molar salt solution including 300 mg bST/l for 37 minutes. The treatment solution was at room temperature. The carp were treated only once and then the length and weight of the carp were followed for several weeks. The weight and length of the carp arc set forth below in Table V and charted in FIGS. 5A and 5B.

TABLE V

Length and Weight of Grass Carp

| | Control Fish | | Treated Fish | |
|---|---|---|---|---|
| Date | Weight (gm) | Length (in) | Weight (gm) | Length (in) |
| 6/29/99 | 0 | 1.1 | 0 | 1.25 |
| 7/13/99 | 0.19 | 1.99 | 0.17 | 2.14 |
| 7/27/99 | 1.15 | 3.61 | 1.32 | 4.06 |
| 8/11/99 | 3.21 | 4.17 | 3.9 | 4.74 |
| 8/26/99 | 4.79 | 6 | 5.99 | 7.1 |
| 9/9/99 | 5.29 | 6.6 | 7.04 | 7.4 |
| 10/14/99 | 10.85 | 7.44 | 17.68 | 9.13 |

Figure 15:
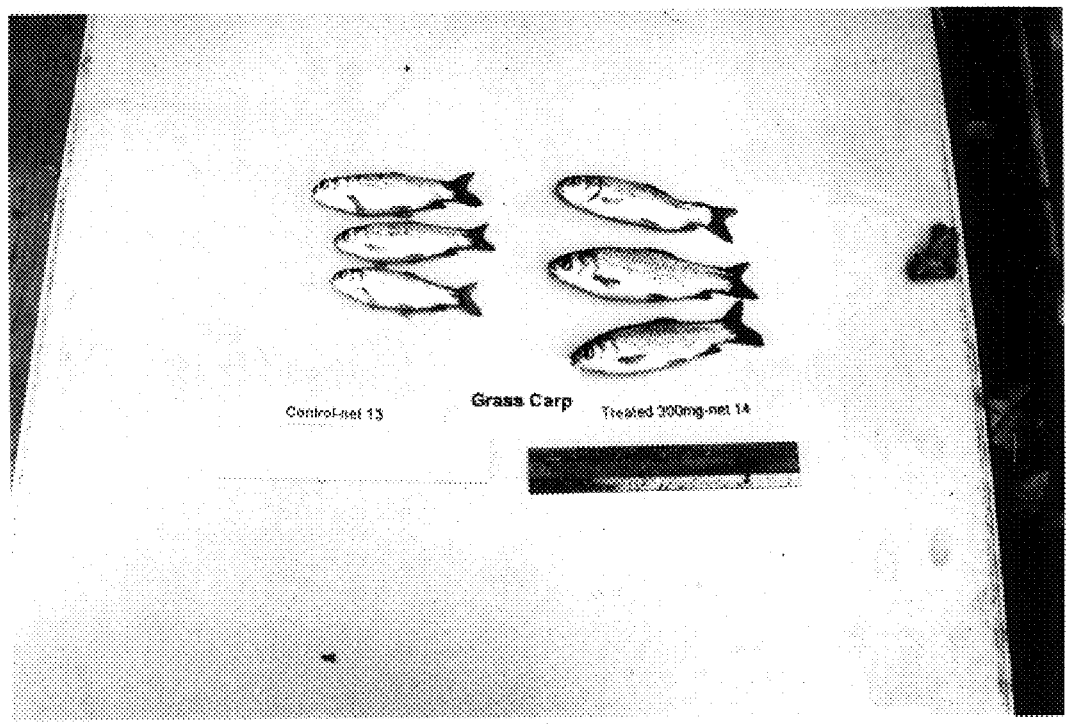
FIG. 15 is a photograph taken in October, 1999 of the control and treated grass carp, the growth of which are charted in FIGS. 5A and 5B.

As can be seen, after slightly more than two months, the treated grass carp weighed approximately 1.75 gm or about 33% more than the control fish and were about 0.8" or about 12% longer than the control fish. After about 3½ months, the treated grass carp weighed about 6.8 gms (or about 63%) more than the control grass carp. The photograph in FIG. 15 shows the differences between the control and treated fish. Analysis of the results using a T-test showed that the data was extremely statistically significant, with a $p<0.001$.

EXAMPLE VI

Treatment of Shrimp

Figure 6A:
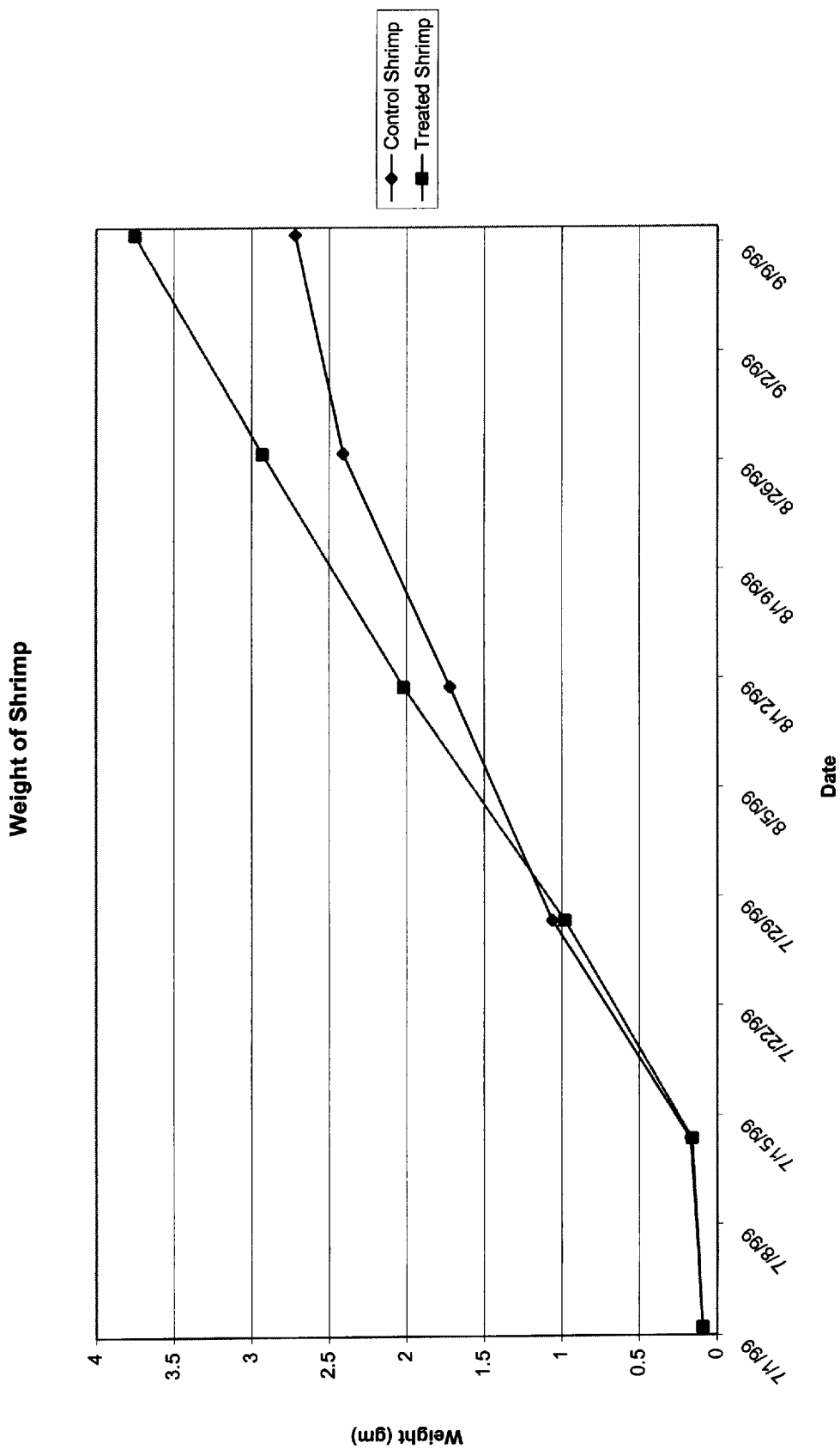
FIGS. 6A and 6B are charts showing the weight and length of shrimp treated with a growth hormone solution of 300 mg growth hormone/liter.
Figure 6B:
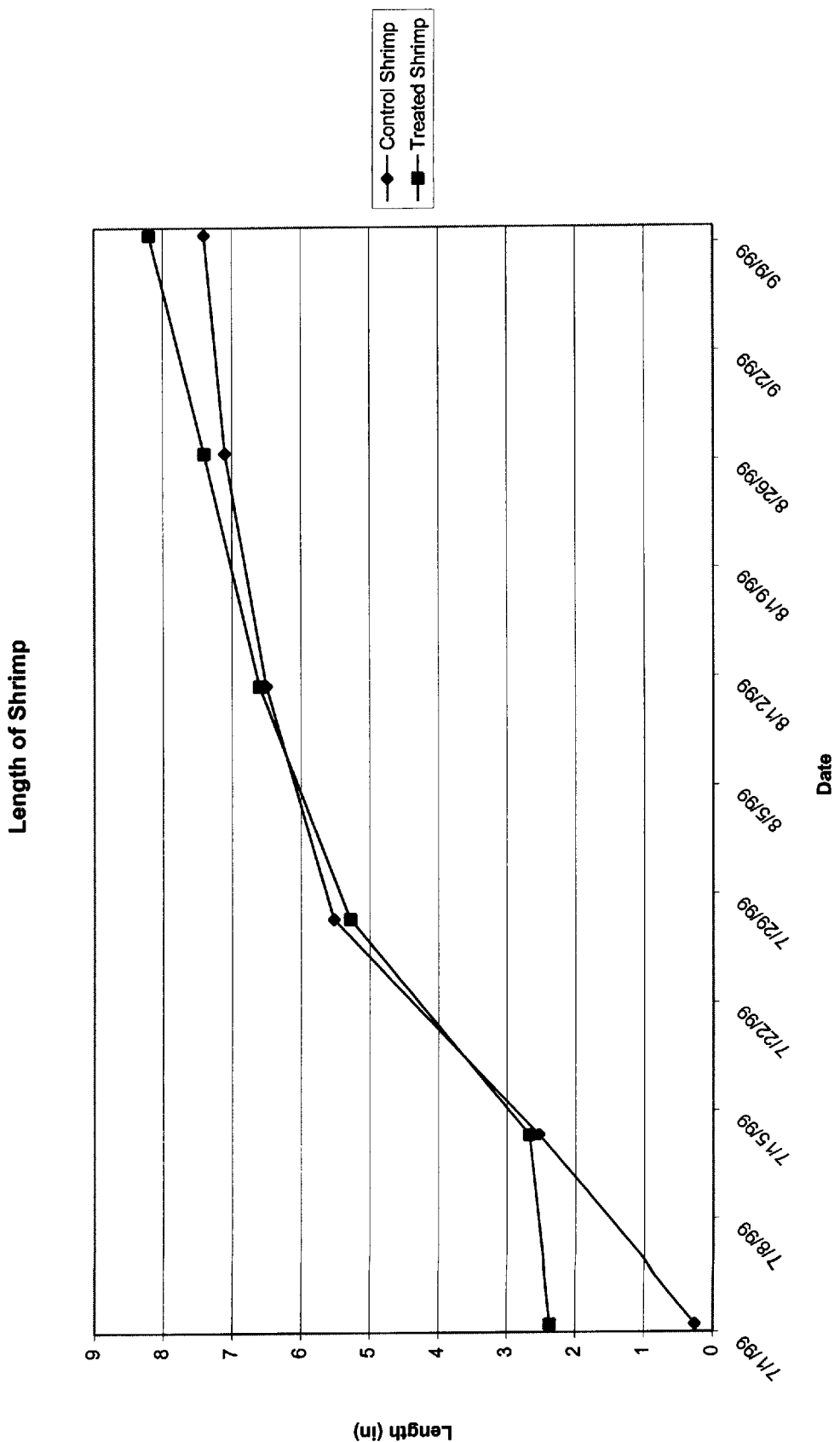

Shrimp were received in a brine solution having a specific gravity of 1.002. The specific gravity of the solution was increased to 1.010 by adding salt to the solution. Growth hormone (bST) in an amount of 300 mg/l was added to the solution, so that the shrimp were osmotically shocked and treated simultaneously. The shrimp were immersed in the treatment solution for one hour, after which time they were removed and returned to a bath having a specific gravity of 1.002. The shrimp were treated only once, and their growth was monitored for several weeks. The weight and length of the shrimp is set forth below in TABLE VI and shown in FIGS. 6A and 6B.

TABLE VI

Single Treatment Of Shrimp

| | Control Shrimp | | Treated Shrimp | |
|---|---|---|---|---|
| Date | Weight (gms) | Length (in) | Weight (gm) | Length (in) |
| 7/1/99 | 0.09 | 0.26 | 0.09 | 2.37 |
| 7/13/99 | 0.17 | 2.53 | 0.16 | 2.67 |
| 7/27/99 | 1.06 | 5.52 | 0.98 | 5.28 |
| 8/11/99 | 1.72 | 6.5 | 2.02 | 6.6 |
| 8/26/99 | 2.41 | 7.1 | 2.93 | 7.4 |
| 9/9/99 | 2.72 | 7.4 | 3.75 | 8.2 |

As can be seen, after about two months, the treated shrimp weighted approximately 1.03 gms or about 38% more than the control shrimp and were about 0.8" or about 11% longer than the control shrimp. Analysis of the results using a T-test shows a statistical significance of $p<0.05$.

EXAMPLE VII

Treatment Of Fish When Less Than 24 Hours Old

In this example, newly born or hatchling catfish were treated. The catfish that were treated were less than 24 hours old, and still had their egg sacs attached to them. The fish were treated once following substantially the same protocol as set forth in Example I (i.e., osmotic shock, immersion for one hour in a saline solution with bST), and their growth was followed for several weeks. The weight and length of the fish are set out below in Table VII and charted in FIGS. 7A and 7B. The fish were divided into four groups. The first group was a control group. This group was subject only to the osmotic shocking solution. The second shocked group, was subject to the osmotic shocking solution and then immersed for one hour in a saline solution having the same salinity as the treatment solution. In the third group, the fish were immersed for one hour in a saline solution having 30 mg bST/l; and in the fourth group, the fish were immersed for one hour in a saline solution having 300 mg bST/l. Analysis of the results using a T-test showed that the data was statistically significant, with a p<0.05.

TABLE VII

| Date | Control fish | Shocked fish | Treated 30 mg bST | Treated 300 mg bST |
|---|---|---|---|---|
| Weight in grams | | | | |
| 6/17/99 | 0.01 | 0.01 | 0.01 | 0.01 |
| 7/16/99 | 0.2 | 0.3 | 0.41 | 0.27 |
| 7/30/99 | 1.19 | 1.57 | 1.91 | 1.56 |
| 8/13/99 | 3.37 | 3.96 | 4.87 | 4.21 |
| 8/26/99 | 5.29 | 5.58 | 6.51 | 7.09 |
| 9/9/99 | 7.65 | 7.19 | 7.41 | 8.95 |
| 10/7/99 | | 11.18 | 12.09 | 21.02 |
| Length In Inches | | | | |
| 6/17/99 | 1.8 | 1.85 | 1.97 | 1.87 |
| 7/16/99 | 2.78 | 3.05 | 3.37 | 3.04 |
| 7/30/99 | 4.99 | 5.45 | 5.88 | 5.45 |
| 8/13/99 | 7.14 | 7.94 | 8.13 | 7.42 |
| 8/26/99 | 8.4 | 8.5 | 9.18 | 8.7 |
| 9/9/99 | 9.3 | 9.5 | 9.5 | 9.7 |
| 10/7/99 | | 10.9 | 11.6 | 13.2 |

Figure 7A:
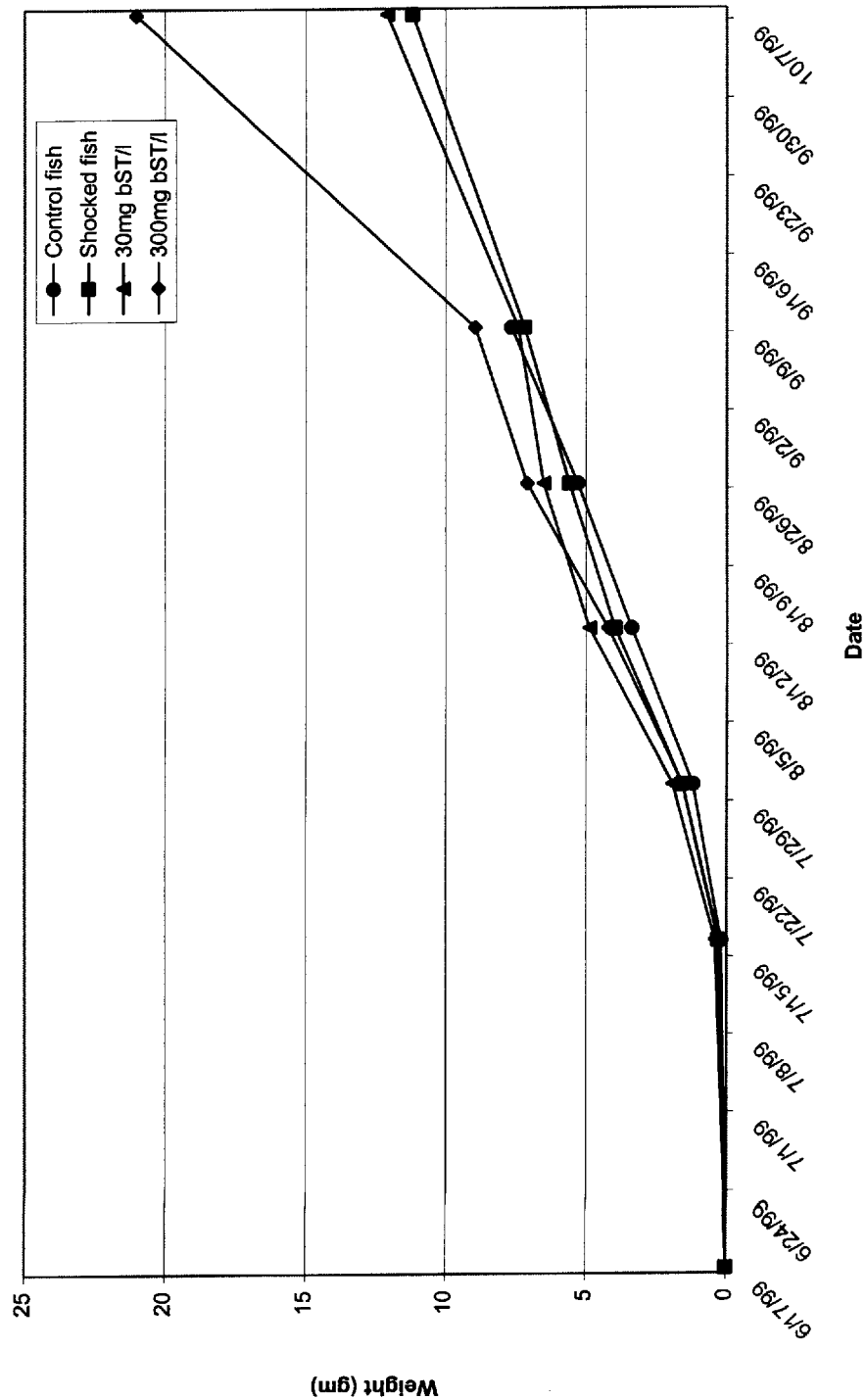
FIGS. 7A and 7B are charts showing the effect of treating embryonic catfish with growth hormone solutions of 30 mg and 300 mg growth hormone per liter of water.
Figure 7B:
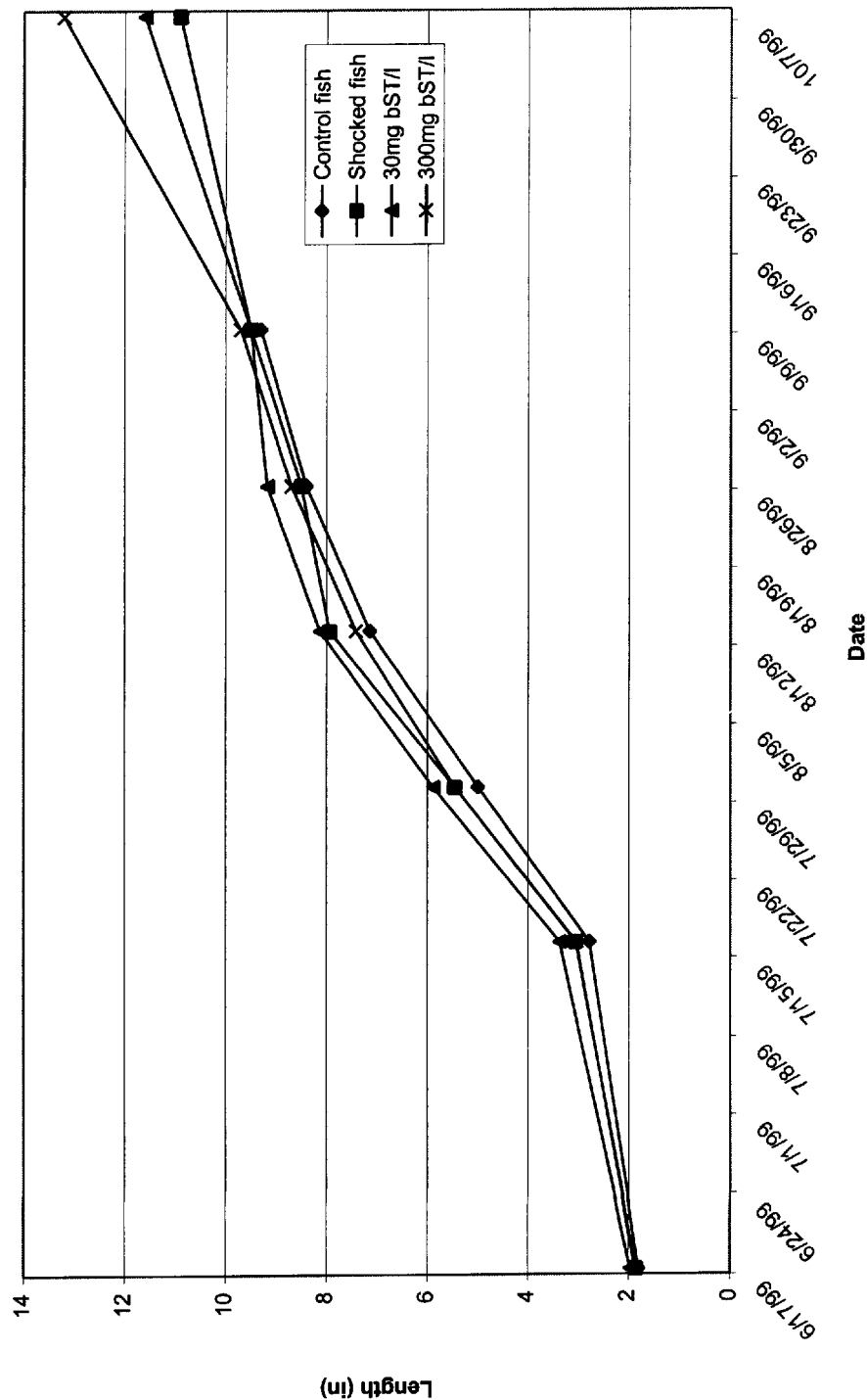
Figure 16:
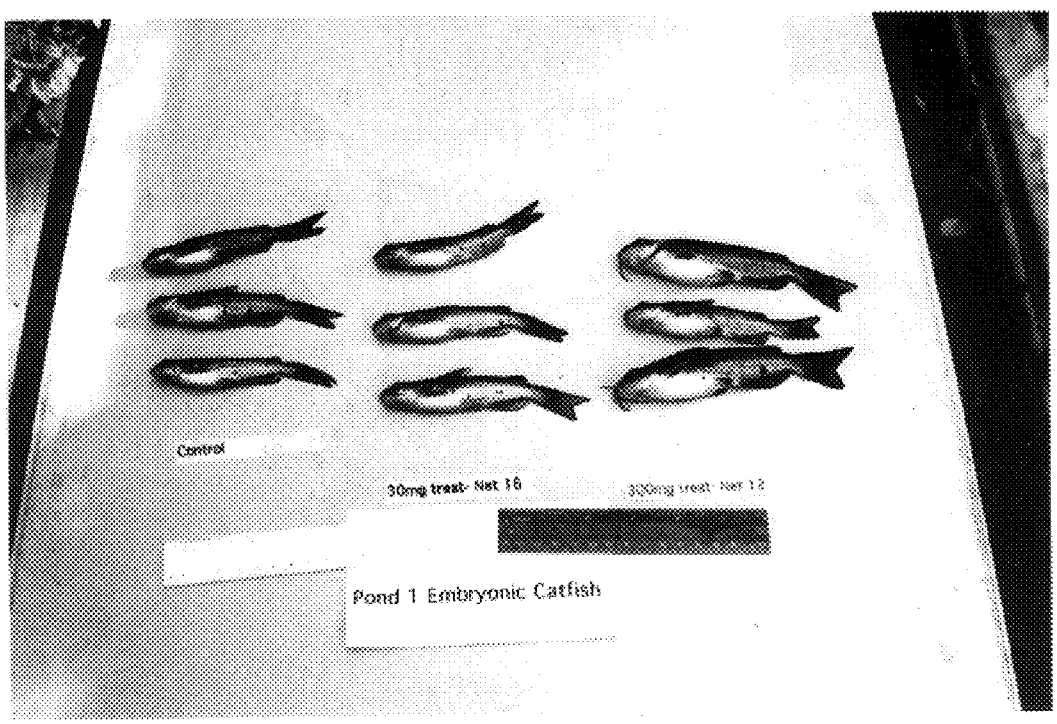
FIG. 16 is a photograph taken in October, 1999 of the control catfish and catfish which were treated as hatchlings, the growth of which is charted in FIGS. 7A and 7B.

As noted above, these fish were treated only once, and when they were very young (less than 24 hours old). This allowed for the treatment many more fish at once, than, for example, if the fish are treated when they are older, for example, six months old. This example shows the increased effect of using a 300 mg/l bST solution over a 30 mg/l bST solution. The fish treated with 30 mg/l weighed less than the control fish (but more than the shocked fish) after almost three months. As compared to the shocked fish, after almost four months, the fish treated with 30 mg bST/l weighed 0.91 gm or about 8% more than the shocked fish and were equal in length to the shocked fish. On the other hand, the fish treated with 300 mg/l bST grew at an overall much faster rate than the fish treated with 30 mg bST. Interestingly, as seen in FIG. 7A, initially the fish treated with 30 mg bST grew at a faster rate than the fish treated with 300 mg bST. However, after about 9 weeks, the rate of growth of the fish treated with 300 mg bST far surpassed the fish treated with 30 mg bST, and the fourth group of fish caught up with, and out grew the third group of fish. At the end of about almost four months, the fish treated with 300 mg bST weighed 9.84 gm or almost 90% more than the shocked fish and weighed 8.91 gm or almost 75% more than the fish treated with 30 mg bST. With respect to length, the fish from all four groups had lengths that were fairly equal at the end of three months. However, in the fourth months, greater differences began to be seen. The fish treated with 30 mg bST/l were about 0.5" longer than the shocked fish and the fish treated with 300 mg bST were about 2.3" and 1.6" longer than the shocked fish and the fish treated with 30 mg bST, respectively. The photograph in FIG. 16 clearly shows the differences between the different groups of fish.

As discussed above, prior articles discussed treating fish with small doses of growth hormone. This example shows that treatment with higher doses of growth hormone dramatically increases the rate at which the fish grow. Analysis of the results using a T-test showed that the data was statistically significant, with a p<0.05 for the fish treated with the 300 mg bST/l solution and a p<0.10 for the fish treated with the 30 mg bST/l solution. Thus, despite the small difference in average weight and length between the control fish and the fish treated with the 30 mg bST/l solution, the lower dosage did have some effect.

EXAMPLE VIII

Effect Food Restriction on the Treatment of Fish

In this example, the fish were divided into four groups. In each group, the food given to the fish was limited. The fish received 10% of their body weight in food daily. The fish were fed three times/day. Thus, at each feeding, the fish received food equal to about 3.33% of their body weight. The first group is a control group in which the fish were not treated with bST. The second group was treated twice; the first time as hatchlings (i.e., less than 24 hours old) and the second time at one month of age; the third group was treated a single time at one month of age; and the fourth group is treated only once as hatchlings. The fish that were treated were treated substantially in accordance with the procedure of Example I. The weight and length of the fish are tabulated below, and charted in FIGS. 8A and 8B.

TABLE VIII

| | Control | | Treated Twice as hatchling and at one month | | Treated Once at One Month of Age | | Treated Once At Embryonic Stage | |
|---|---|---|---|---|---|---|---|---|
| Date | Wt (gm) | Length (in) | Wt (gm) | Length (in) | Wt (gm) | Length (in) | wt (gm) | Length (in) |
| 6/17/99 | 0.01 | 1.8 | 0.01 | 1.87 | 0.01 | 1.8 | 0.01 | 1.87 |
| 7/16/99 | 0.2 | 2.75 | 0.27 | 3.04 | 0.2 | 2.75 | 0.27 | 3.04 |
| 7/21/99 | 0.51 | 3.56 | 0.58 | 3.82 | 0.42 | 4.03 | 0.55 | 4.61 |
| 8/5/99 | 1.29 | 5.28 | 1.39 | 5.48 | 1.34 | 5.36 | 1.51 | 5.6 |
| 8/12/99 | 2.03 | 6.12 | 2.07 | 6.28 | 2.12 | 6.25 | 2.32 | 6.43 |
| 8/19/99 | 2.68 | 6.7 | 2.65 | 6.7 | 2.64 | 6.6 | 3.28 | 7.1 |
| 8/31/99 | 4.59 | 8 | 4.23 | 7.8 | 4.17 | 7.69 | 4.88 | 8.2 |

TABLE VIII-continued

| | Control | | Treated Twice as hatchling and at one month | | Treated Once at One Month of Age | | Treated Once At Embryonic Stage | |
|---|---|---|---|---|---|---|---|---|
| Date | Wt (gm) | Length (in) | Wt (gm) | Length (in) | Wt (gm) | Length (in) | wt (gm) | Length (in) |
| 9/10/99 | 6.08 | 8.7 | 5.73 | 8.6 | 5.05 | 8.2 | 6.49 | 8.9 |
| 9/16/99 | 6.93 | 8.9 | 6.67 | 9.2 | 5.66 | 8.5 | 7.58 | 9.4 |
| 9/23/99 | 10.14 | 9.9 | 8.45 | 9.6 | 7.32 | 8.9 | 9.52 | 9.8 |
| 9/30/99 | 12.54 | 10.8 | 11.28 | 10.3 | 10.29 | 9.8 | 11.97 | 10.7 |
| 10/7/99 | 17.18 | 11.9 | 13.87 | 11.4 | 12.35 | 10.8 | 17.14 | 11.9 |
| 10/14/99 | 19.77 | 12.9 | 16.33 | 12.2 | 14.84 | 11.7 | 18.99 | 12.6 |

Although the data trend appears to show differences between the groups of fish, the weight in each group of fish varied widely. Thus, analysis of the results showed no statistical significance between the groups. From my observations, it is believed that the treated fish have larger appetites than the untreated fish. Thus, as the fish consume more food, with an increased metabolism rate, they will grow larger in size.

Figure 8A:
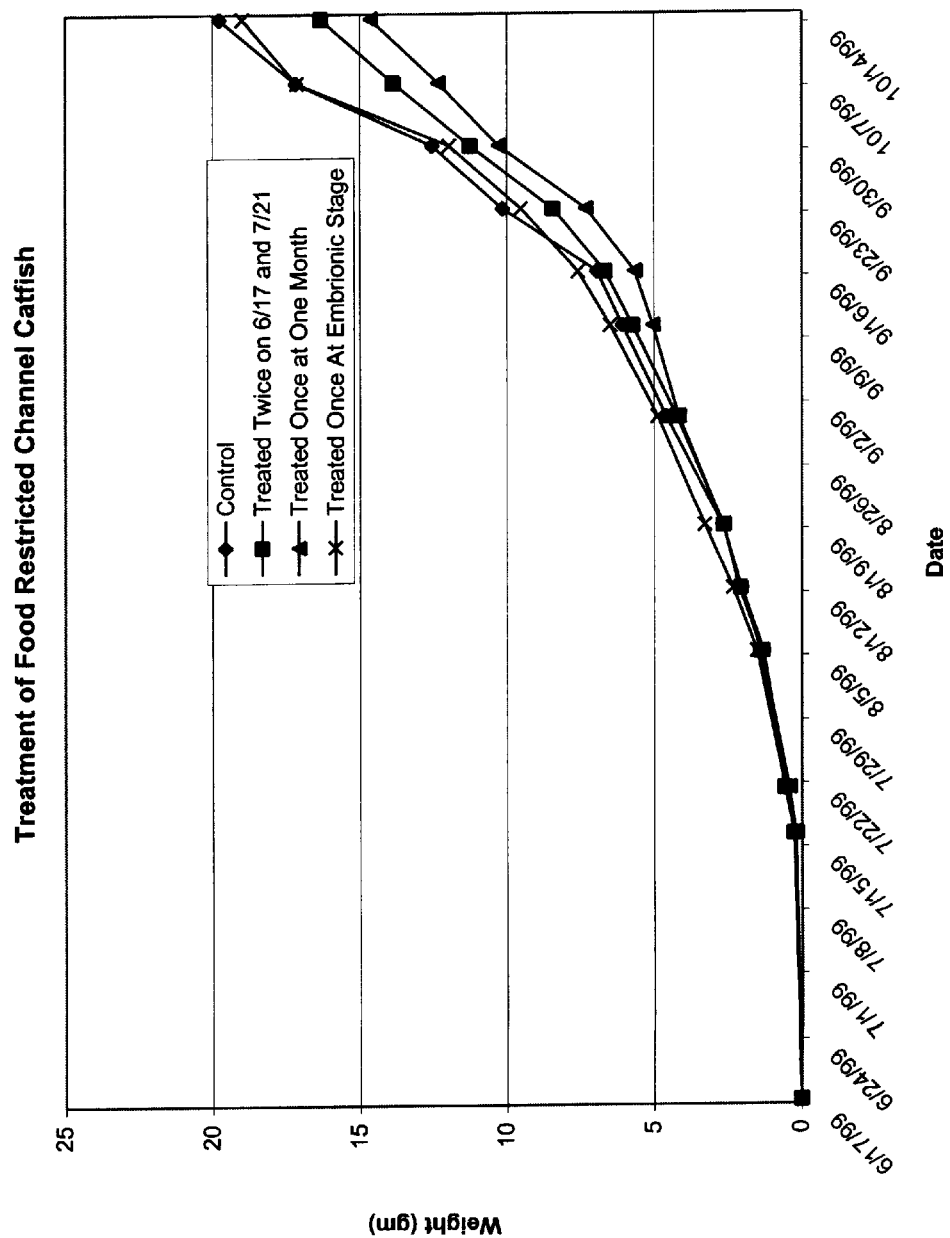
FIGS. 8A and 8B are charts showing weight and length of catfish wherein the fish were treated once, twice, as hatchlings, and as older fish; the chart also shows the effect of limiting the food intake of the fish.
Figure 8B:
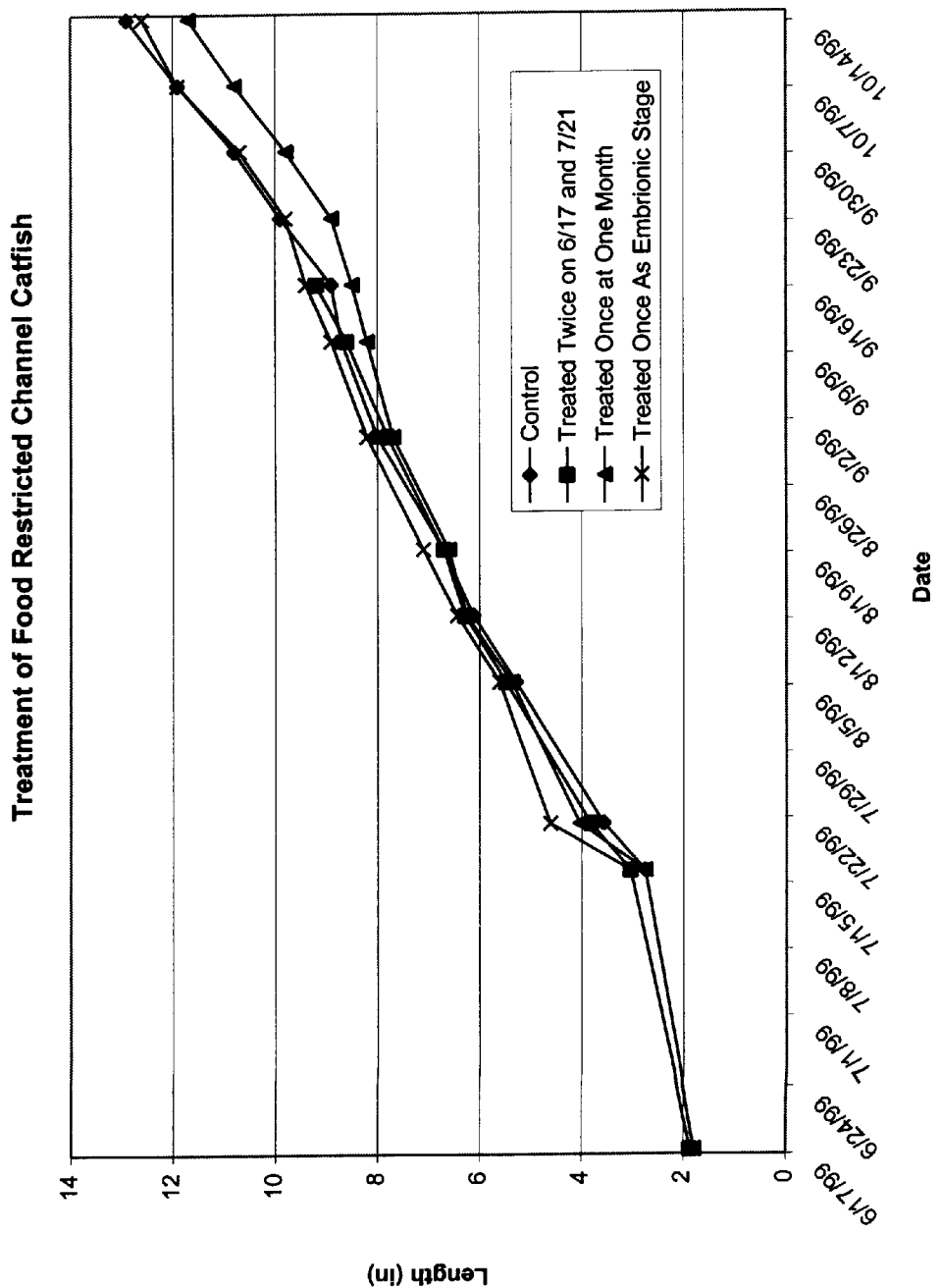

With respect to the trends of the data in the charts (i.e., the averages shown in the charts) treatment of fish only once as hatchlings (i.e., less then 24 hours old), once when about one month in age, or twice—as hatchlings and again at one month, it can be seen that the fish treated as hatchlings were larger after four months than the fish treated only at one month of age. Thus, it is beneficial to treat the fish at a younger age. Additionally, the fish treated only once as hatchlings were larger at the end of the test than the fish treated twice. Thus, the additional treatment did not cause the fish to grow faster. In fact, for some reason, the additional treatment of the fish appears to have slowed down the rate of growth of the fish, such that the fish in the control group were able to catch up in weight with the fish treated twice. Additionally, as seen in FIG. 8A, the treatment of the fish only once at one month of age did not significantly affect the rate of growth of the fish, as compared to the control group.

Figure 17:
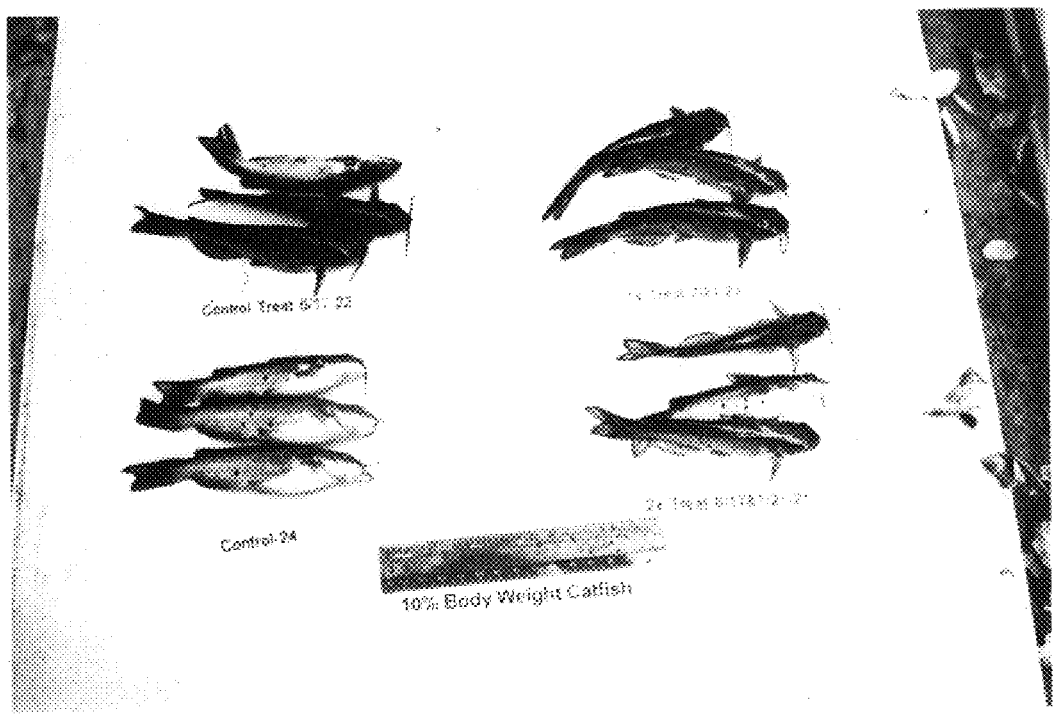
FIG. 17 is a photograph taken in October, 1999 of the control fish, the fish treated once, and the fish treated twice, the growth of which are charted in FIGS. 8A and 8B.

From this, it can be seen that the bST best affects the growth rate of young fish. It apparently has little to no effect on older fish (i.e., one month of age), except as administered in higher shock and treatment solutions. Thus, the preferred time for treating the fish is when they are hatchlings. Because hatchlings are much smaller than when they are one month old, many more hatchlings than older fish can be treated at once in a given volume of solution. Because of the expense of the bST, it is also preferred to be able to maximize the number of fish that can be treated simultaneously. The photograph in FIG. 17 shows the similarities and differences between the treatment groups.

EXAMPLE IX

Varying Immersion Time In The Treatment Solution And bST Dosage

In this test, the effect of the time in which hybrid striped bass were immersed in the treatment solution was tested, as well as varying bST concentrations. The bass were placed in treatment solutions of 30 mg bST/l and 300 mg bST/l for varying amounts of time. It was determined that immersing the fish according to the present protocol (i.e., osmotic shock and immersion in an oxygenated saline/bST solution) for more than about two hours was detrimental to the fish's health. It is believed that the bST binds to the fish's gills and inhibits oxygen transfer across the fish's gills. Thus, the immersion time in the treatment solution is preferably less than two hours. The results for 1½-hour and 1-hour immersion (or treatment) are shown below in Table IX and charted in FIG. 9. The fish were divided into seven groups. There was one control group, three groups for the 1½ hour treatment and three groups for the 1 hour treatment The three groups for the 1½ hour and 1 hour treatment each included a control shock group (a group of fish which were immersed in a saline solution having a salinity equal to the salinity of the treatment solution), a group of fish which were placed in a 30 mg bST/l solution, and a group of fish which were placed in a 300 mg bST/l solution.

TABLE IX

Weight of Fish for Varying Immersion Times And Doses of bST

| | | 1½ Hour Treatment | | | 1 Hour Treatment | | |
|---|---|---|---|---|---|---|---|
| Date | Control | Control Shock | 30 mg bST | 300 mg bST | Control Shocked | 30 mg | 300 mg |
| 6/25/99 | 0.62 | 0.62 | 0.62 | 0.62 | 0.62 | 0.62 | 0.62 |
| 7/9/99 | 1.63 | 2.19 | 1.94 | 1.85 | 1.95 | 1.94 | 1.95 |
| 7/23/99 | 3.86 | 5.67 | 6.02 | 6.12 | 6.15 | 5.15 | 5.88 |
| 8/6/99 | 7.64 | 11.05 | 10.72 | 11.28 | 10.93 | 9.68 | 10.89 |
| 8/19/99 | | 18.71 | 19.37 | 22.94 | 20.52 | 18.85 | 19.98 |
| 9/2/99 | | 25.29 | 25.21 | 29.11 | 26.37 | 23.14 | 24.96 |
| 9/16/99 | | 29.06 | 29.41 | 40.12 | 31.19 | 29.45 | 29.85 |
| 10/14/99 | | 37.57 | 42.96 | 43.14 | 38.82 | 38.78 | 41.78 |

Figure 9:
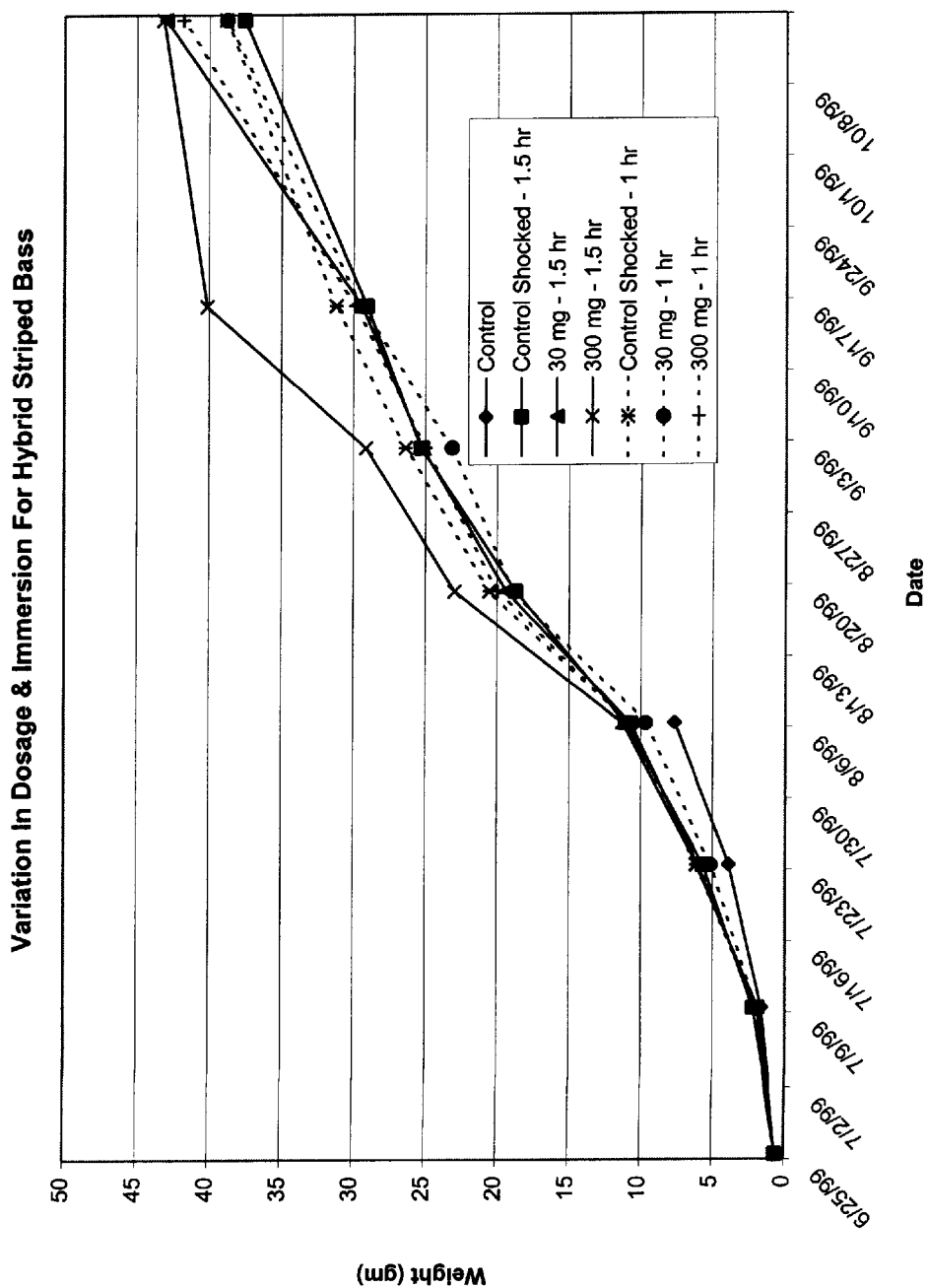
FIG. 9 is a chart showing the weight of bass in which the bass were subject to different immersion times and to different dosages of growth hormone solution.
Figure 13:
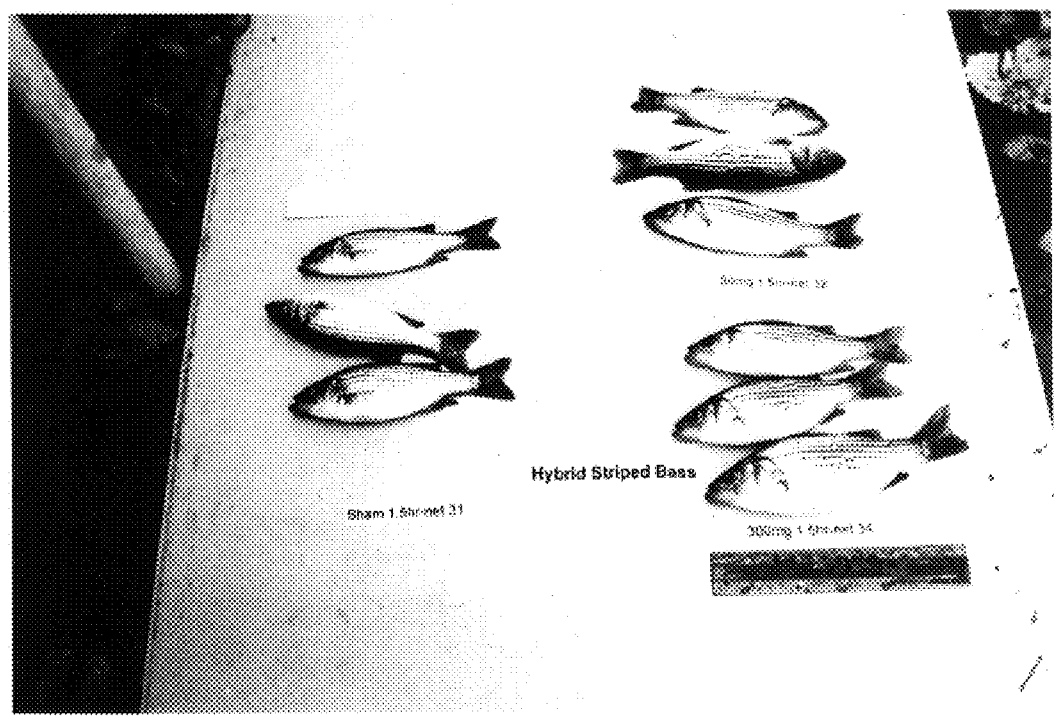
FIG. 13 is a photograph taken in October, 1999 of the control and treated hybrid striped bass treated for 1½ hours in solutions of 30 mg bST/l and 300 mg bST/l, the growth of which is charted in FIG. 9.
Figure 14:
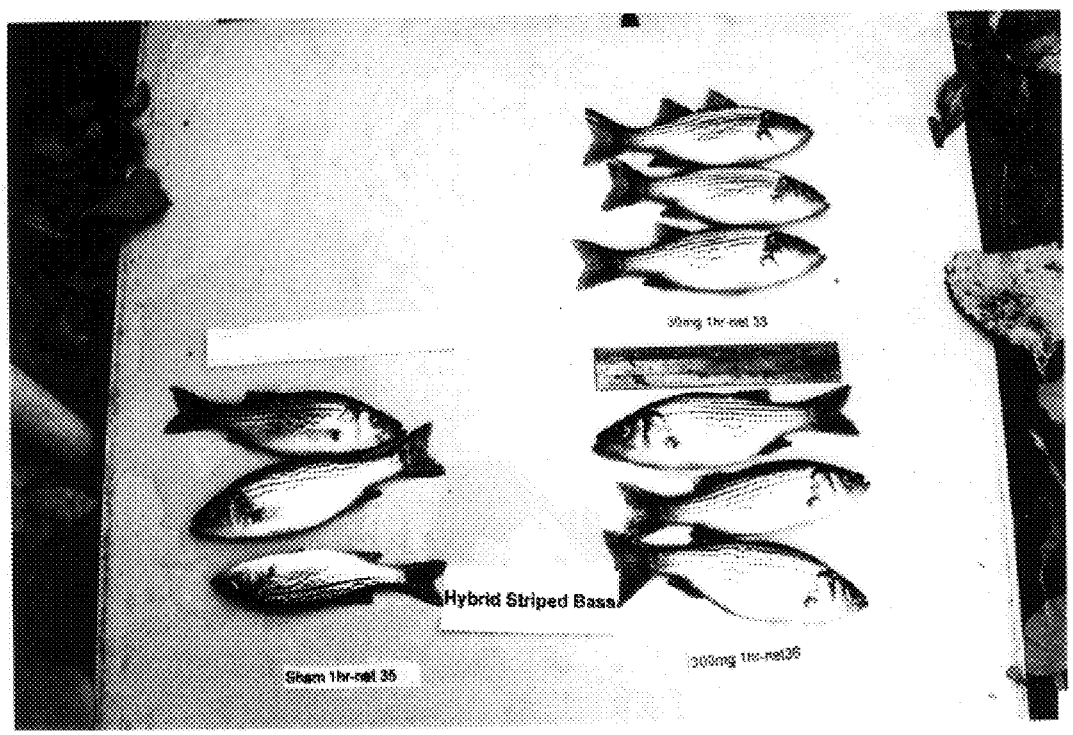
FIG. 14 is a photograph taken in October, 1999 of the control and treated hybrid striped bass treated for 1 hour in solutions of 30 mg bST/l and 300 mg bST/l, the growth of which is charted in FIG. 9.

As can be seen from the results in Table IX and from the chart of FIG. 9, the was no significant increase in the weight of fish treated with 30 mg bST when they were immersed for 1½ hours, as compared to the shocked fish at the end of three months. At the end of four months, however, the fish treated with the 30 mg/l bST solution weighed 5.39 gm, or about 14%, more than the shocked fish. For the 1 hour treatment, it can be seen that there is no marked difference between the control shocked group and the group treated with the 30 mg bST/l solution. In fact, at the end of nearly four months, the fish treated with the 30 mg bST/l solution for one hour weighed nearly as much on average as their control shocked fish. Thus, the extra one-half hour in the 30 mg bST/l solution appears to have allowed the fish to absorb more bST, such that fish treated for 1½ hours do show a faster growth rate than the control fish. However, when the fish were treated for both 1½ hours and 1 hour, there was a significant increase in weight gain between the fish treated with 30 mg bST and the fish treated with 300 mg bST. There was a marked increase in the weight gain of the fish treated with 300 mg bST over the fish treated with 30 mg bST. At the end of three months, the fish treated with 300 mg bST for 1½ hours weighed about 36% more than the fish treated with 30 mg bST. And at the end of four months, the fish treated with 300 mg bST weighted only about 0.4% more than the fish treated with 30 mg bST. In the intervening month, the fish treated with 30 mg bST/l grew at a faster rate, and substantially caught up with the fish treated with the 300 mg bST/l solution. For the fish treated for 1 hour, at the end of three months, there was not much difference between the weight of the fish treated with 300 mg bST/l and the fish treated with 30 mg bST/l. However, during the fourth month, the fish treated with 300 mg bST/l grew at a much faster rate, and weighted 3 gm (or about 7%) more than the fish treated with 30 mg bST/l. Thus, higher concentrations (up to a point, as discussed below) appear to create higher growth rates earlier. The differences between the groups can be visually seen in the photographs in FIGS. 13 and 14. Analysis of the results using a T-test showed statistical significance at a $p<0.05$.

EXAMPLE X

High Dosage of bST

Figure 10A:
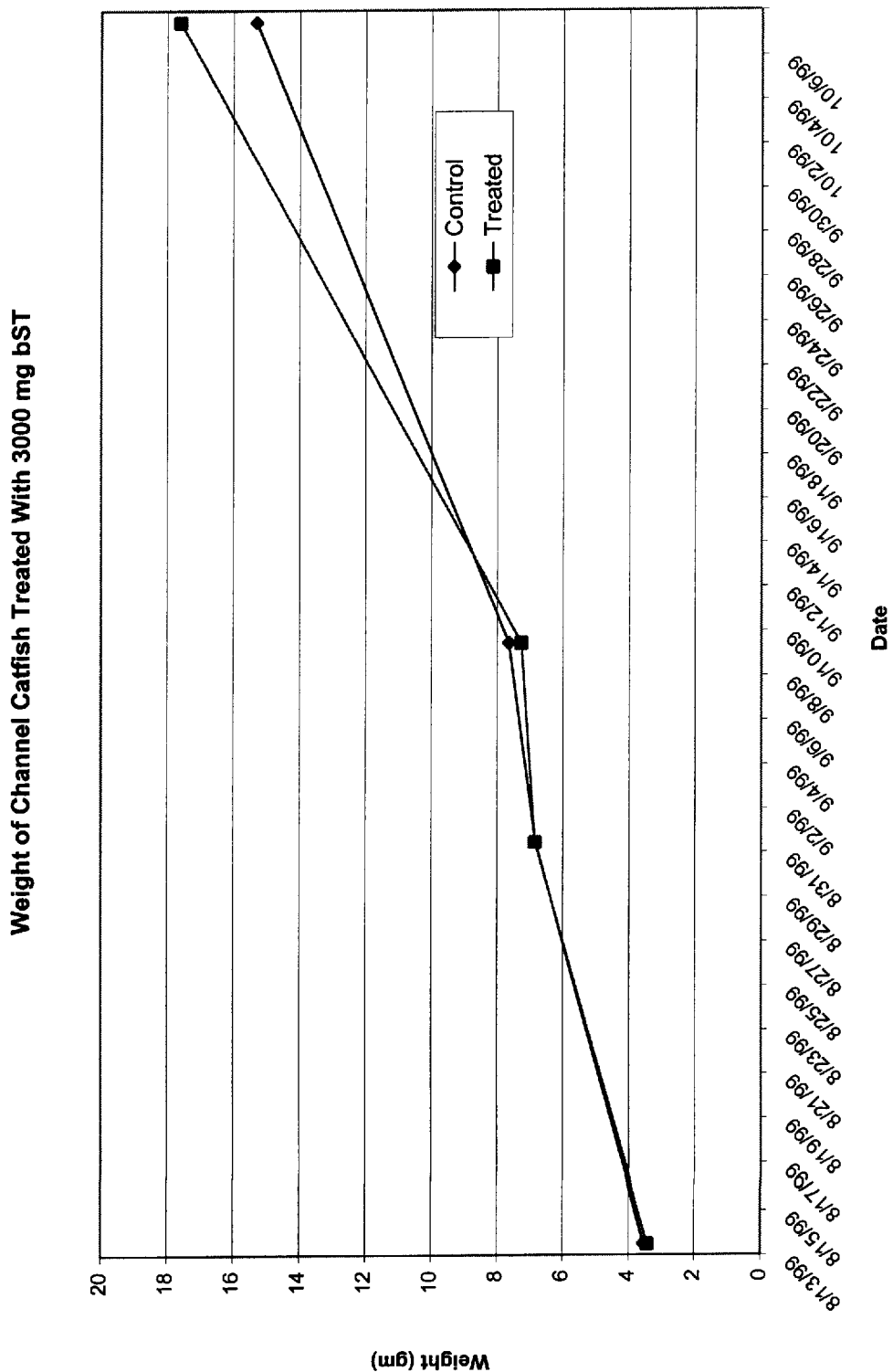
FIGS. 10A and 10B are charts showing the weight and length of catfish treated with high levels of growth hormone.
Figure 10B:
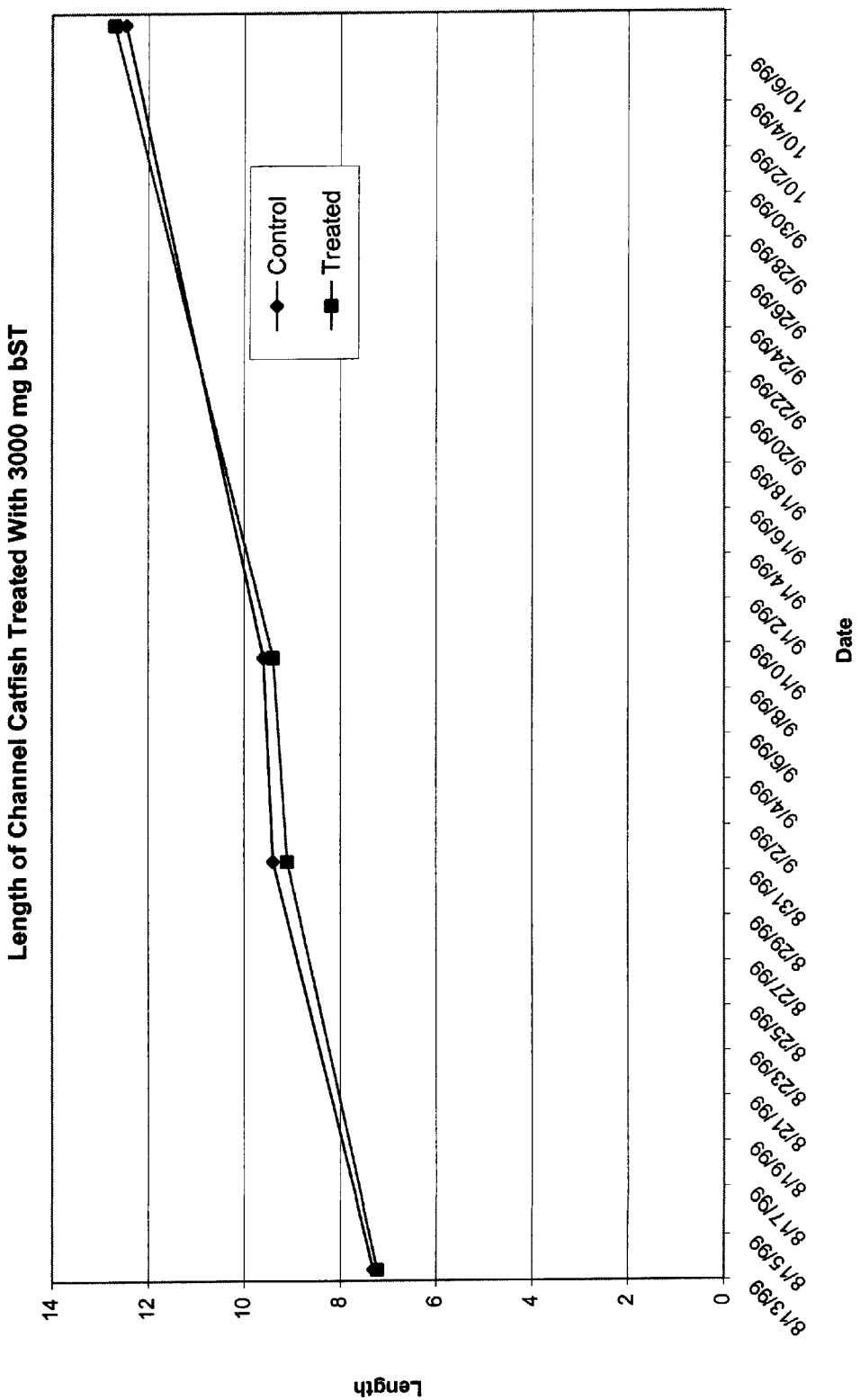
Figure 12:
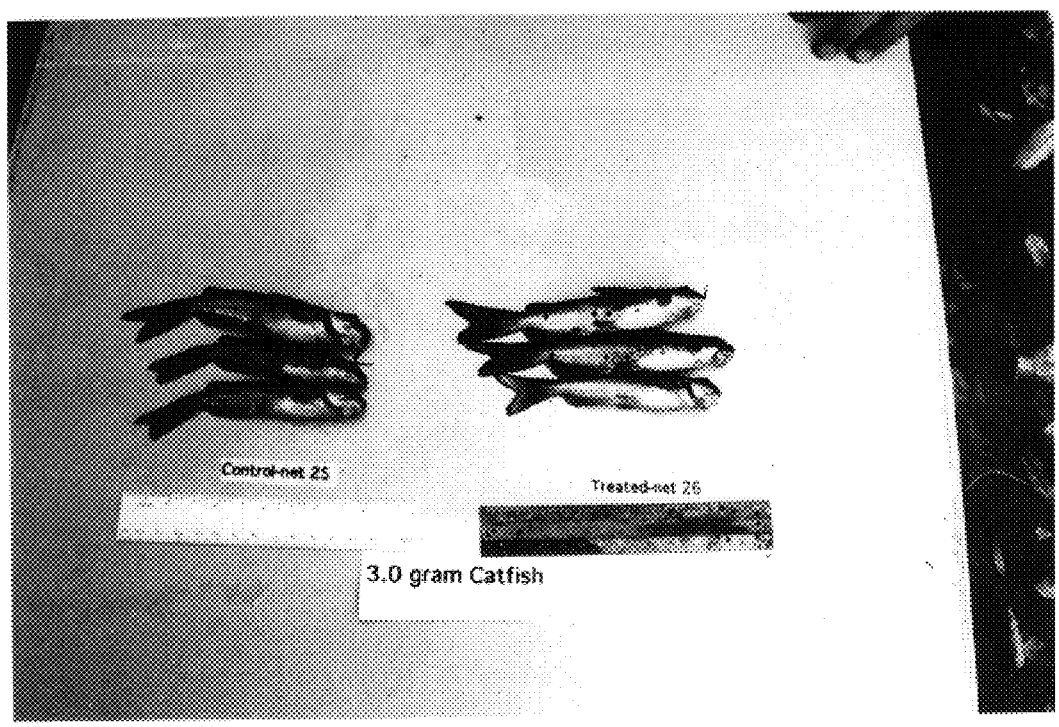
FIG. 12 is a photograph taken in October, 1999 comparing the size of control fish with fish treated with 3 gm bST/l, and showing that the treated fish were significantly different in size from the control fish, the growth of which is charted in FIGS. 10A and 10B.

In this test, the fish were subject a treatment solution containing 3000 mg bST/l of solution. The fish treated where less than 24 hours old, and were immersed in the treatment solution for one hour. As can be seen in Table X below and in the charts of FIGS. 10A and 10B, the fish immersed in the 3000 mg/l bST treatment solution did not grow any faster or any larger than the fish in the control group by the end of the third month. However, by the end of the fourth month, the treated fish were somewhat larger than the control fish. As seen in Table X, the treated fish weighed about 2.3 gm or 15% more than the control fish. Analysis of the results using a T-test showed statistical significance at a $p<0.05$. The effects of the high dosage treatment can be seen visually in the photograph in FIG. 12.

TABLE X

| | Control | | Treated | |
|---|---|---|---|---|
| Date | weight (gms) | length (in) | weight (gm) | length (in) |
| 8/13/99 | 3.54 | 7.31 | 3.43 | 7.23 |
| 8/31/99 | 6.83 | 9.4 | 6.85 | 9.1 |

TABLE X-continued

| | Control | | Treated | |
|---|---|---|---|---|
| Date | weight (gms) | length (in) | weight (gm) | length (in) |
| 9/9/99 | 7.64 | 9.6 | 7.26 | 9.4 |
| 10/7/99 | 15.31 | 12.45 | 17.61 | 12.7 |

EXAMPLE XI

Treatment of Coho Salmon

Figure 11:
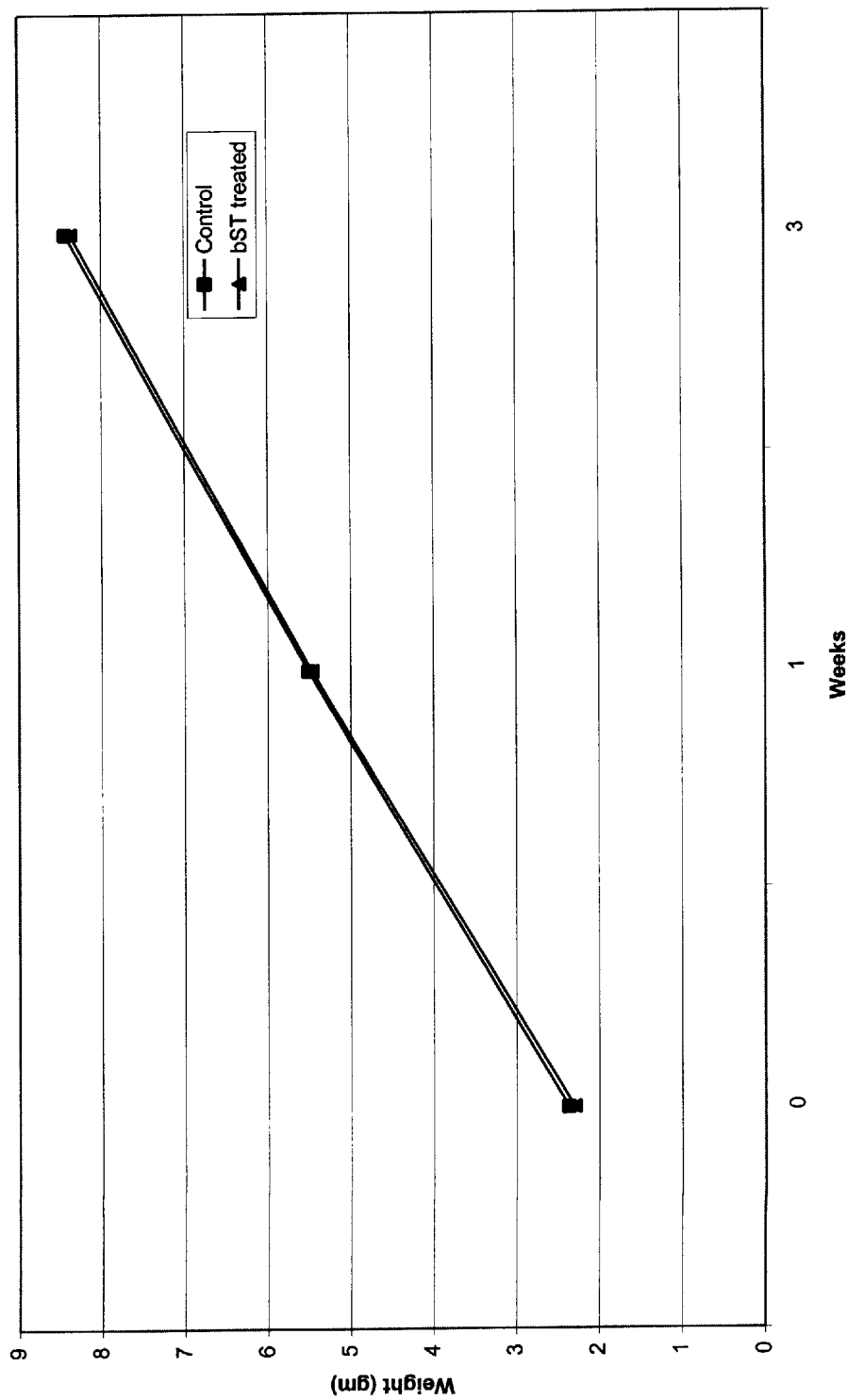
FIG. 11 is a chart showing the weight gain of treated coho salmon v. untreated coho salmon.

In this test, coho salmon were treated in accordance with Example I (osmotic shock, treatment solution containing 300 mg bST/l of solution for one hour). As can be seen in Table XI below and in the charts of FIG. 11, the coho salmon which were treated with bST did not grow at a rate faster than the coho salmon in the control group. As noted above, prior studies showed that the treatment of coho salmon was effective. Therefore, it is hypothesized that the treatment techniques I designed are wholly different from previously conducted research.

TABLE XI

| Week | Control | bST treated |
|---|---|---|
| 0 | 2.37 | 2.3 |
| 1 | 5.51 | 5.47 |
| 3 | 8.43 | 8.37 |

Conclusion

As can be seen, by immersing aquatic animals in solutions having a high concentration of bST, the growth rate of these aquatic animals can be dramatically increased. This will enable aquaculturists to grow, and thus harvest, the aquatic animals more quickly, thereby effectively increasing the amount of cultured food available to feed people and decrease subsistence on wild caught food sources.

Although the method was described with respect to the administration of growth honnones, and in particular, bST, to aquatic animals, it is believed that the method of administering bST to the aquatic animals, as set forth above, will work equally well with other pharmaceutically active agents which are absorbed through the gut of the aquatic animal. Namely, as set out above, the aquatic animal is initially shocked in a hyperosmotic saline solution and then immersed in a solution of the pharmaceutically active agent for a desired period of time. Obviously, the concentration of the treatment solution will vary depending on the pharmaceutically active agent being administered. The concentration will have to be sufficient so that the aquatic animal absorbs a sufficient amount of the pharmaceutically active agent during the immersion period in the solution. If longer treatment periods are desired or needed, the treatment solution can be supersaturated with oxygen to place the aquatic animal in a state of suspended animation.

As various changes could be made in the above treatment method without departing from the scope of the invention, it is intended that all matter contained in the above description shall be interpreted as illustrative and not in a limiting sense. For example, the treatment solution could be supersaturated with oxygen prior to placing the fish in the treatment tank. Although bST was used as the growth hormone, other growth hormones, which are similar in molecular structure to the bST, should work equally as well. This example is merely illustrative.

What is claimed is:

1. A method of increasing the rate of growth of aquatic animals, comprising immersing the aquatic animals in a treatment solution for a desired period of time of less than four hours; the treatment solution consisting essentially of a growth hormone in a saline solution; the treatment being administered only a single time, the aquatic animals being treated when they are less than five days old.

2. The method of claim 1 wherein the treatment solution has about 3 to 3000 mg growth hormone per liter.

3. The method of claim 1 wherein the treatment solution has about 150 to 450 mg growth hormone per liter.

4. The method of claim 1 wherein the treatment solution has about 300 mg growth hormone per liter.

5. The method of claim 1 wherein the growth hormone is bST.

6. The method of claim 1 wherein prior to immersing the aquatic animals in the treatment solution, the aquatic animals are osmotically shocked in a hyperosmotic saline solution.

7. The method of claim 1 wherein the treatment solution is supersaturated with oxygen.

8. A method of administering growth hormone to aquatic animals comprising the steps of:
   (a) osmotically shocking the aquatic animals with a osmotic salt solution;
   (b) placing the shocked aquatic animals in a treatment tank containing a solution of growth hormone for a predetermined period of time, the solution being refrigerated; and
   (c) supersaturating the growth hormone solution with oxygen while the aquatic animals are in the treatment tank.

9. The method of claim 8 wherein the aquatic animals are osmotically shocked for about 120 seconds.

10. The method of claim 8 wherein the growth hormone solution contains about 3–3000 mg growth hormone/l.

11. The method of claim 8 wherein the aquatic animals remain in the growth hormone solution for about 2 minutes to about 2 hours.

12. The method of claim 11 wherein the aquatic animals remain in the growth hormone solution for about sixty to about 90 minutes.

13. The method of claim 8 wherein the method further includes a step of raising the temperature of the aquatic animals to an ambient temperature after the predetermined period of time has lapsed by increasing the temperature of the solution.

14. The method of claim 8 wherein the temperature of the growth hormone solution is about 450° F.

15. The method of claim 8 wherein the steps (a)–(c) are repeated every two weeks.

16. The method of claim 8 wherein the aquatic animals are treated only once.

17. The method of claim 16 wherein the aquatic animals are treated before 6 months of age.

18. The method of claim 17 wherein the aquatic animals are treated when less than 9 days old.

19. The method of claim 18 wherein the aquatic animals are treated when less than 24 hours old.

20. A method of administering growth hormone to aquatic animals comprising the steps of immersing aquatic animals in a growth hormone solution for at least thirty minutes, the solution being contained in a closed tank, and placing the tank under a pure oxygen atmosphere while the aquatic animals are immersed in the growth hormone solution.

21. The method of claim 20 including supersaturating the growth hormone solution with oxygen.

22. A method of administering a pharmaceutically active agent to an aquatic animal; the method including:
   shocking the aquatic animal in a hyperosmotic saline solution; and
   immersing the aquatic animal in a treatment solution of the pharmaceutically active agent; and
   supersaturating the treatment solution with oxygen.

23. The method of claim 1 wherein the temperature of the treatment solution is about 45° F.

* * * * *

UNITED STATES PATENT AND TRADEMARK OFFICE
CERTIFICATE OF CORRECTION

PATENT NO. : 6,238,706 B1
DATED : May 29, 2001
INVENTOR(S) : Leonard Sonnenschein It is certified that error appears in the above-identified patent and that said Letters Patent is hereby corrected as shown below:

Column 6,
Line 50, replace "tlu—ee" with -- three --;

Column 8,
Line 60, replace "weighted" with -- weighed --;

Column 13,
Line 2, replace "Figure 9, the" with -- Figure 9, there --;
Lines 25 and 34, replace "weighted" with -- weighed --;
Line 44, replace "subject a treatment" with -- subjected to a treatment --

Column 16,
Line 10, replace "450° F." with -- 45° F. --

Signed and Sealed this

Twenty-third Day of April, 2002

Attest:

JAMES E. ROGAN
*Attesting Officer*     *Director of the United States Patent and Trademark Office*